US010617480B2

(12) United States Patent
Brisson

(10) Patent No.: US 10,617,480 B2
(45) Date of Patent: *Apr. 14, 2020

(54) TELE-OPERATIVE SURGICAL SYSTEMS AND METHODS OF CONTROL AT JOINT LIMITS USING INVERSE KINEMATICS

(71) Applicant: Intuitive Surgical Operations, Inc., Sunnyvale, CA (US)

(72) Inventor: Gabriel F. Brisson, Sunnyvale, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/201,887

(22) Filed: Nov. 27, 2018

(65) Prior Publication Data

US 2019/0105117 A1 Apr. 11, 2019

Related U.S. Application Data

(63) Continuation of application No. 15/126,967, filed as application No. PCT/US2015/020889 on Mar. 17, 2015, now Pat. No. 10,188,471.

(Continued)

(51) Int. Cl.
*A61B 34/35* (2016.01)
*G05B 19/427* (2006.01)
(Continued)

(52) U.S. Cl.
CPC .............. *A61B 34/35* (2016.02); *A61B 34/30* (2016.02); *B25J 9/1607* (2013.01); *B25J 9/1689* (2013.01);
(Continued)

(58) Field of Classification Search
CPC ... A61B 34/35; A61B 2090/031; A61B 34/76; A61B 34/30; A61B 90/03; B25J 9/1607;
(Continued)

(56) References Cited

U.S. PATENT DOCUMENTS 5,184,601 A  2/1993  Putman et al.
5,445,166 A  8/1995  Taylor et al.
(Continued)

FOREIGN PATENT DOCUMENTS

CN  103230301 A  8/2013
CN  103429398 A  12/2013
(Continued)

OTHER PUBLICATIONS

International Search Report and Written Opinion for Application No. PCT/US15/20889, dated Jun. 8, 2015, 18 pages.
(Continued)

*Primary Examiner* — Jaime Figueroa
(74) *Attorney, Agent, or Firm* — Artegis Law Group, LLP

(57) ABSTRACT

Devices, systems, and methods for controlling manipulator movements include a manipulator arm coupled to a proximal base. The manipulator arm is configured to support an end effector and robotically move the end effector relative to the proximal base. The manipulator arm includes a plurality of joints between the end effector and the proximal base and a processor. The processor is configured to calculate joint movements of the plurality of joints that provide a desired position of the end effector using inverse kinematics of the manipulator arm and when a first set of one or more joints of the plurality of joints is at corresponding joint range of motion limits: determine a constraint based on a relationship between joint movement of the first set and a second set of
(Continued)

one or more joints of the plurality of joints and apply the constraint within the inverse kinematics to provide haptic feedback.

20 Claims, 25 Drawing Sheets

Related U.S. Application Data

(60) Provisional application No. 61/954,568, filed on Mar. 17, 2014.

(51) Int. Cl.
*A61B 34/30* (2016.01)
*B25J 9/16* (2006.01)
*A61B 34/00* (2016.01)
*A61B 90/00* (2016.01)

(52) U.S. Cl.
CPC ............ *G05B 19/427* (2013.01); *A61B 34/76* (2016.02); *A61B 90/03* (2016.02); *A61B 2090/031* (2016.02); *G05B 2219/40381* (2013.01); *G05B 2219/45119* (2013.01)

(58) Field of Classification Search
CPC ......... B25J 9/1689; G05B 2219/45119; G05B 19/427; G05B 2219/40381
USPC .......................................................... 700/245
See application file for complete search history.

(56) References Cited

U.S. PATENT DOCUMENTS

| | | | |
|---|---|---|---|
| 5,737,500 A | 4/1998 | Seraji et al. | |
| 5,800,423 A | 9/1998 | Jensen et al. | |
| 5,808,665 A | 9/1998 | Green | |
| 5,855,583 A | 1/1999 | Wang et al. | |
| 6,246,200 B1 | 6/2001 | Blumenkranz et al. | |
| 6,676,669 B2 | 1/2004 | Charles et al. | |
| 6,699,177 B1 | 3/2004 | Wang et al. | |
| 6,702,805 B1 | 3/2004 | Stuart et al. | |
| 6,714,839 B2 | 3/2004 | Salisbury, Jr. et al. | |
| 6,758,843 B2 | 7/2004 | Jensen et al. | |
| 6,786,896 B1 | 9/2004 | Madhani et al. | |
| 7,594,912 B2 | 9/2009 | Cooper et al. | |
| 7,725,214 B2 | 5/2010 | Diolaiti | |
| 7,763,015 B2* | 7/2010 | Cooper .................. | A61B 90/10 606/1 |
| 8,004,229 B2 | 8/2011 | Nowlin et al. | |
| 8,271,130 B2 | 9/2012 | Hourtash et al. | |
| 8,624,537 B2* | 1/2014 | Nowlin .................. | B25J 9/1682 318/568.21 |
| 8,768,516 B2 | 7/2014 | Diolaiti et al. | |
| 8,918,207 B2 | 12/2014 | Prisco et al. | |
| 9,687,310 B2* | 6/2017 | Nowlin .................. | B25J 9/1682 |
| 1,018,847 A1 | 1/2019 | Brisson et al. | |
| 2005/0027397 A1 | 2/2005 | Niemeyer | |
| 2007/0142825 A1 | 6/2007 | Prisco et al. | |
| 2007/0156122 A1 | 7/2007 | Cooper | |
| 2009/0326318 A1* | 12/2009 | Tognaccini ........ | A61B 1/00183 600/104 |
| 2010/0274087 A1 | 10/2010 | Diolaiti et al. | |
| 2011/0290856 A1* | 12/2011 | Shelton, IV ........... | A61B 34/71 227/180.1 |
| 2012/0132450 A1* | 5/2012 | Timm .................. | A61B 17/072 173/47 |
| 2012/0179169 A1 | 7/2012 | Swarup et al. | |
| 2012/0191247 A1 | 7/2012 | Kishi | |
| 2012/0245736 A1 | 9/2012 | Bosscher et al. | |
| 2013/0053866 A1 | 2/2013 | Leung et al. | |
| 2013/0175969 A1 | 7/2013 | Kwon et al. | |
| 2014/0039681 A1 | 2/2014 | Bowling et al. | |
| 2014/0052155 A1 | 2/2014 | Hourtash et al. | |
| 2014/0222207 A1 | 8/2014 | Bowling et al. | |
| 2017/0095301 A1 | 4/2017 | Brisson | |

FOREIGN PATENT DOCUMENTS

| | | |
|---|---|---|
| DE | 19800552 A1 | 1/1999 |
| JP | H06312392 A | 11/1994 |
| KR | 20130080638 A | 7/2013 |
| WO | WO-2006124390 A2 | 11/2006 |
| WO | WO-2008094766 A2 | 8/2008 |
| WO | WO-2012121125 A1 | 9/2012 |
| WO | WO-2012133913 A1 | 10/2012 |

OTHER PUBLICATIONS

Extended European Search Report for Application No. EP15764523.5, dated Oct. 23, 2017, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Flacco F., et al., "Motion Control of Redundant Robots Under Joint Constraints: Saturation in the Null Space," IEEE International Conference on Robotics and Automation, May 2012, pp. 285-292.
Maneewarn T., et al., "Augmented Haptics of Manipulator Kinematic Condition," Proceedings of SPIE, Nov. 1999, vol. 3840, pp. 54-64.

* cited by examiner

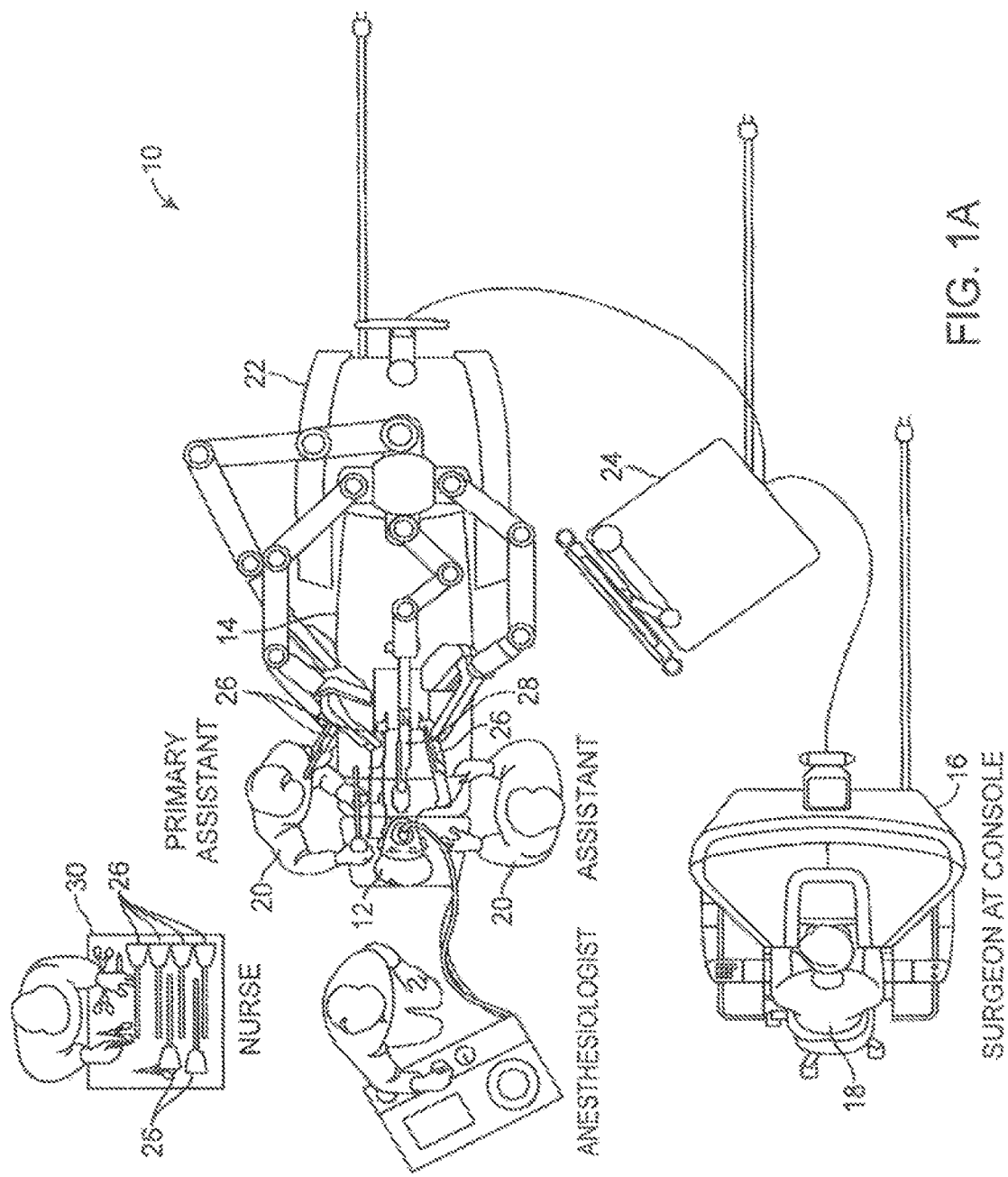

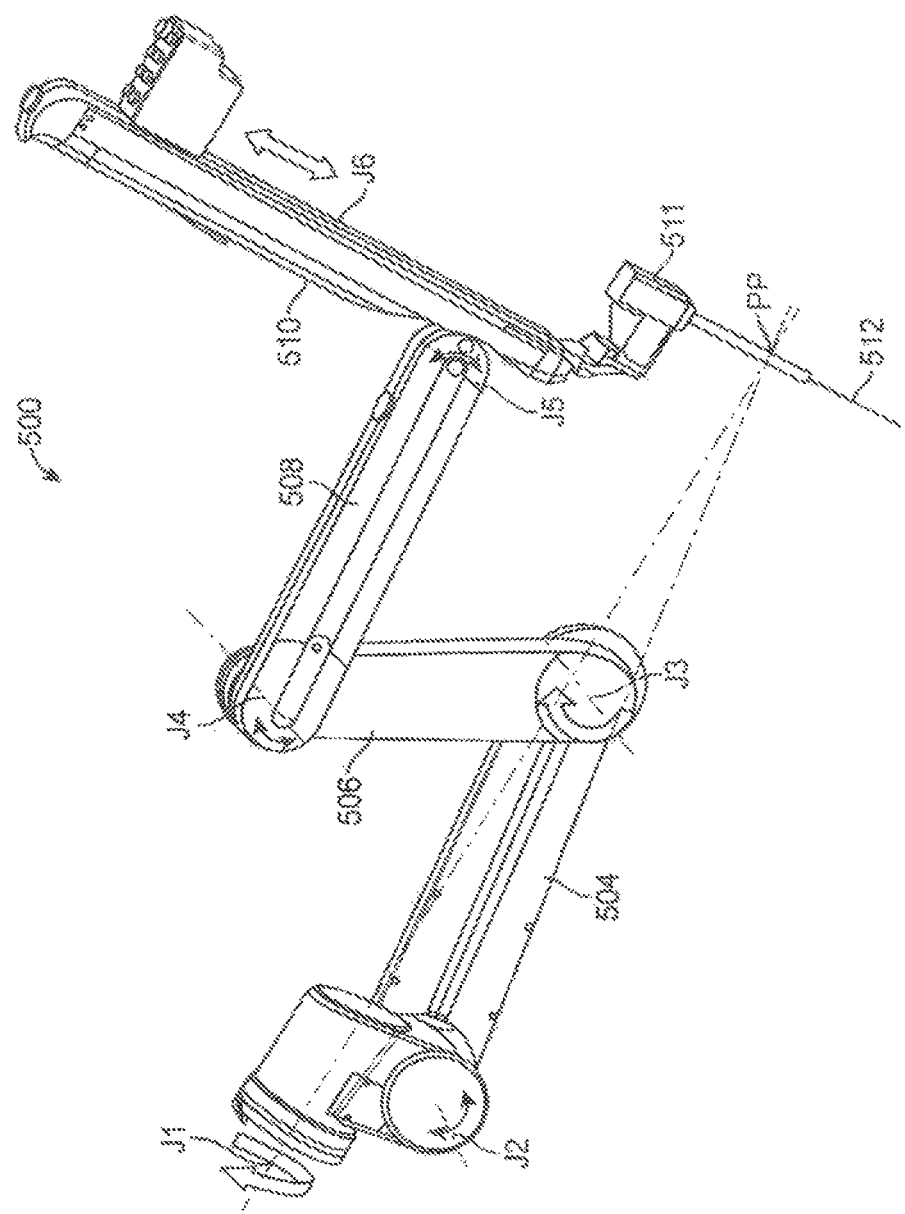

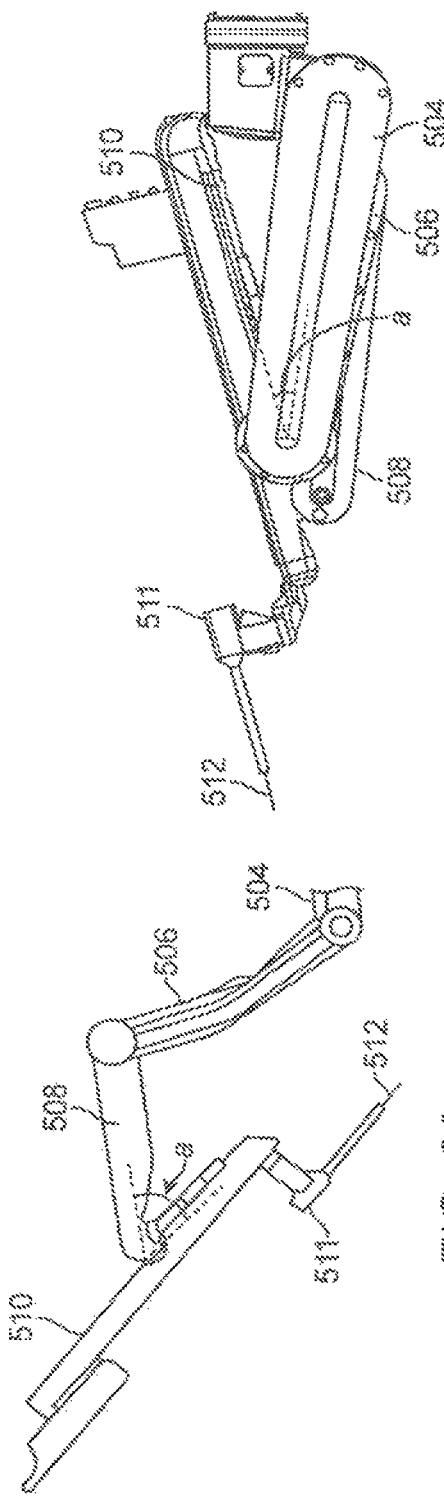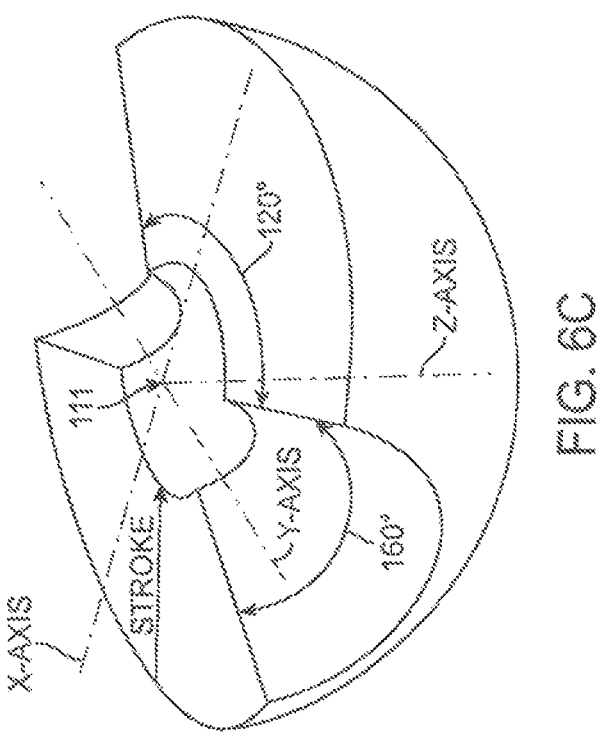

TELE-OPERATIVE SURGICAL SYSTEMS AND METHODS OF CONTROL AT JOINT LIMITS USING INVERSE KINEMATICS

CROSS-REFERENCES TO RELATED APPLICATIONS

The present application is a continuation of U.S. patent application Ser. No. 15/126,967 filed on Sep. 16, 2016, which is a U.S. National Stage patent application of International Patent Application No. PCT/US2015/020889, filed on Mar. 17, 2015, which claims priority to U.S. Provisional Application No. 61/954,568 filed Mar. 17, 2014, the entire contents of each of which is incorporated herein by reference.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" U.S. application Ser. No. 09/398,507 filed Sep. 17, 1999 (U.S. Pat. No. 6,714,839), entitled "Master Having Redundant Degrees of Freedom;" U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue that is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, a limited number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example linkage arrangements for use as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, a manipulator arm may include additional redundant joints to provide increased movements or configurations under certain conditions. When moving surgical instruments within a minimally invasive surgical site, however, these joints may exhibit a significant amount of movement outside the patient, often more movement than needed or expected, particularly when pivoting instruments about minimally invasive apertures through large angular ranges. Alternative manipulator structures have been proposed which employ software control over a highly configurable kinematic manipulator joint set to restrain pivotal motion to the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may have safety advantages in some conditions. Additionally, the wide range of configurations of the numerous joints often included in these manipulators may result in the manipulators being difficult to manually set-up in a configuration that is desirable for a particular procedure. Nonetheless, as the range of surgeries being performed using telesurgical systems continues to expand, there is an increasing demand for expanding the available configurations and the range of motion of the instruments within the patient. Unfortunately, both of these changes can increase the challenges associated with the motion of the manipulators outside the body and can occasionally result in unpredictable or unexpected movements of the manipulator due to the increased complexities of such manipulator configurations.

For these and other reasons, it would be advantageous to provide improved devices, systems, and methods for surgery, robotic surgery, and other robotic applications. It would be particularly beneficial if these improved technologies provided the ability to limit the amount of movement of the manipulator arm during certain tasks or to provide improved, more predictable movement of the manipulator. Additionally, it would be desirable to provide such improvements while increasing the range of motion of the instruments for at least some tasks and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In various embodiments, the invention will employ highly configurable surgical robotic manipulators. These manipulators, for example, may have more degrees of freedom of movement than the associated surgical end effectors have within a surgical workspace. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. A manipulator may include additional redundant joints to allow for a range of alternative configurations and movements while effecting a desired movement of a tool tip or end effector. While various manipulators having additional redundant joints are described herein, it is appreciated that aspects of the present invention may also be utilized in non-redundant manipulators as well.

As movement of one or more joints of the manipulator approach and reach an associated joint range of motion (ROM) limit, however, the manipulator can lose the ability to follow the position being commanded by the user on the master controller. To help the user recognize this limitation and return to a position where the manipulator is no longer constrained, it can be useful to provide a feedback force/torque on the master controller that indicates the nature of the limitation. It is desired that this feedback force/torque be in an optimal direction for guiding the user out of the constrained configuration. For example, most manipulator joint limits will create a constraint that involves a combination of translation and rotation. The feedback torque is properly proportioned with respect to the feedback force in order to create feedback that naturalistically expresses the nature of the constraint to the user.

If the master controller implements a control algorithm that displays forces and torques to the user proportionately to the error between the current master position and a virtual slave manipulator position, then the problem of expressing slave joint limits to the user becomes a problem of choosing the virtual slave manipulator position that will generate the appropriate forces and torques for display to the user. In another aspect, if a method uses resolved rate motion, and then just saturates joint positions that come out of that algorithm, then the algorithm may converges to a position that may not provide intuitive force feedback.

The methods described herein may be utilized to calculate appropriate, more intuitive force feedback on a master manipulator when the teleoperated slave manipulator reaches a range-of-motion limit. An example method includes: receiving a first manipulation command to move a distal end effector of a manipulator arm to a desired first position within a workspace, the manipulator arm extending between a proximal base and the distal end effector and including a plurality of joints having sufficient degrees of freedom to allow a range of joint states for a given state of the distal end effector; calculating first joint movements of the plurality of joints that provide the desired first position of the distal end effector using inverse kinematics of the manipulator arm; and locking at least one joint of the plurality of joints when the at least one joint is at a joint range-of-motion (ROM) limit of the at least one joint, wherein locking the at least one joint comprises modifying an input variable within the inverse kinematics that correspond to movement of the at least one joint within the workspace. Locking the joint causes the inverse kinematics algorithm to calculate a position for the slave manipulator, which, when passed to the master manipulator, results in the master manipulator exerting a force/torque that guides the user away from the range-of-motion limit. In another aspect, methods include unlocking one or more locked joints when it is determined that the movement provided by the locked joint, if included in calculated joint movements to effect a desired end effector position, would move away from the respective joint range of motion limit or would move the tool tip toward the goal position.

In another aspect, methods for controlling joint movements when a joint is at its limit so as to express joint limits to a user in a more predictable, intuitive manner are provided. An example method includes: receiving a manipulation command to move a distal end effector of a manipulator arm to a desired position within a workspace, the manipulator arm extending between a proximal base and the distal end effector and including a plurality of joints having sufficient degrees of freedom to allow a range of joint states for a given state of the distal end effector; calculating joint movements of the plurality of joints that provide the desired position of the distal end effector using inverse kinematics of the manipulator arm; determining a constraint based on a relationship between joint movement of a first set of joints and second set of joints; and applying the constraint within the inverse kinematics when the first set of joints is at a joint range of motion (ROM) limit. Each of the first and second set of joints comprises one or more joints. In some embodiments, the relationship is defined between a translational joint movement and a rotational joint movement in the first and second set of joints. In certain embodiments, the relationship is based on a relationship of static loads, such as applied forces and torques, on the first and second joints when the first set of joints reaches its joint ROM limit. In other embodiments, the constraint includes a relationship that conserves a total energy of the joints when one or more joints are locked at their respective joint ROM limit and the total kinetic energy in the joints within the calculated joint movements to effect a desired goal position of a tool tip or end effector without movement of the locked joints. Methods may further include scaling and weighting between certain joints or joint movements, the scaling and weighting be applied within the inverse kinematics to provide the desired joint movement behaviors.

A further understanding of the nature and advantages of the present invention will become apparent by reference to the remaining portions of the specification and drawings.

BRIEF DESCRIPTION OF THE DRAWINGS

FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

FIGS. 5A-5D show an example manipulator arm.

FIGS. 6A-6B show an example manipulator arm in the pitch forward configuration and pitch back configurations, respectively.

FIG. 6C shows a graphical representation of the range of motion of the surgical instrument tool tip of an example manipulator arm, including a cone of silence or conical tool access limit zone in each of the pitch forward and pitch back configurations.

DETAILED DESCRIPTION OF THE INVENTION

Figure 1B:
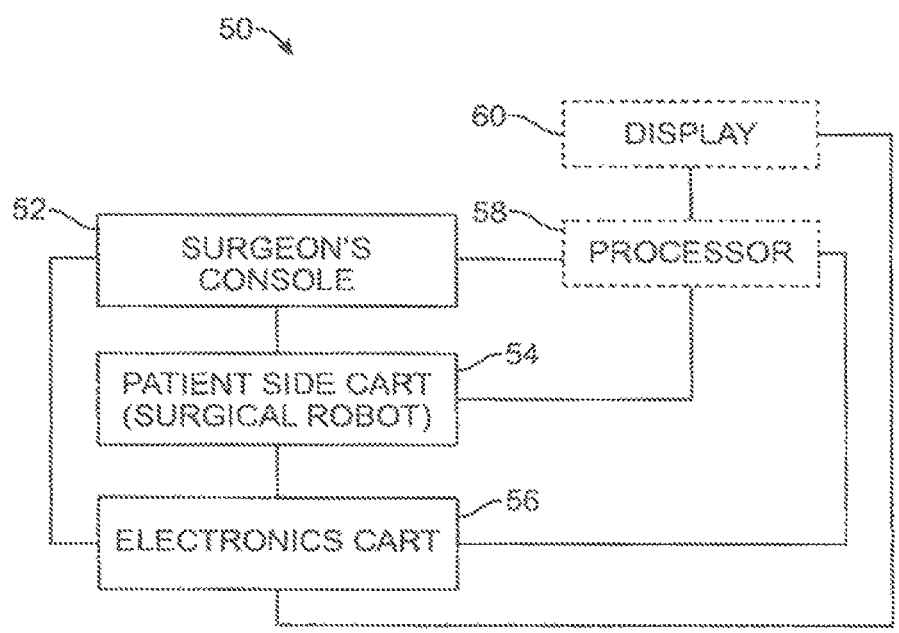
FIG. 1B diagrammatically illustrates the robotic surgical system of FIG. 1A.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. Aspects of a master controller, that may be used in accordance with the methods and systems described herein, are described in U.S. patent application Ser. No. 12/400,728, entitled "Operator Input Device for Robotic Surgical System" filed Mar. 9, 2009 and in U.S. patent application Ser. No. 12/494,695, entitled "Control of Medical Robotic System Manipulator About Kinematic Singularities," filed Jun. 30, 2009, each of which is incorporated herein by reference for all purposes. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom allows a system operator, or an assistant, to reconfigure the linkages of the manipulator assemblies while maintaining the desired end effector state, optionally in preparation for surgery and/or while another user maneuvers the end effector during a surgical procedure.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

In various embodiments, the end effector will move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but may have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In various embodiments, the tool of an example manipulator arm pivots about a pivot point adjacent a minimally invasive aperture. The system may utilize a hardware remote center, such as the remote center kinematics described in U.S. Pat. No. 6,786,896, the entire contents of which are incorporated herein in its entirety. Such systems may also utilize a double parallelogram linkage which constrains the movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site would appear to offer few or any improvements in the range of motion. Nonetheless, such joints can provide significant advantages by allowing the overall system to be configured in or driven toward a collision-inhibiting pose by further extending the range of motion for other surgical procedures, and the like. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a calculated pivot point, as opposed to a pivot point defined by a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

A fundamental tool in controlling movement of the highly configurable manipulator is the kinematics equations of the kinematic chains that form the manipulator arm. Typically, these equations are used to map the joint parameters to the configuration of the robot system. Forward kinematics is the use of kinematic equations of the manipulator arm to compute the position of a a feature of the manipulator in the workspace, typically a distal tool tip or end effector, from specified values of the joint parameters. The reverse process, known as inverse kinematics, can be used to compute joint parameters that achieve a specified position of the feature, typically a desired tool tip position. The dimensions of the manipulator arm and its associated kinematic equations define the volume of space reachable by the manipulator, known commonly as the workspace. Typically, in response to a command to move the tool tip to a desired position, inverse kinematics are used to compute associated joint angles of joint of the manipulator that achieve the desired tool tip position. The time derivative of the kinematics equations yields the Jacobian of the manipulator, which relates the joint rates to the linear and angular velocity of the tool tip or end effector as well as a relationship between joint torques and a resultant force and torque applied by the end effector. Inverse kinematics can be performed in a hard-coded manner such that joint angles are related to a Cartesian coordinate position according to a particular equation of an associated kinematic chain. The primary drawback of this hard-coded approach is that the hard-coded equations would not apply to different kinematic chains or if the kinematic chain was modified. Another approach for applying inverse kinematics is the use of numerical inverse kinematics, which is adaptable to any kinematic chain. Numerical inverse kinematics may utilize resolved rate motion, gradient descent and calculation of Jacobian matrix.

While numerical inverse kinematics is advantageous in this aspect, one drawback is that joint movement when effected may result in impaired or undesirable movements when one or more joints of the manipulator are at their respective joint ROM limits, such that the joints do not attain the desired tool tip position. In addition, when a portion of the manipulator utilizes combined joint movements, such as translation and rotation, provided by coupled joints, when one of the coupled joints is at its respective joint limit, the resulting movement at the master may appear counter-intuitive to a user. In another example, one may apply an iterative algorithm (e.g. resolve rate motion) and saturate intermediate solutions found by this algorithm, however suturing the ROM-limit joint will affect the solution that the other joints converge to and may result in non-intuitive movements of the manipulator and/or at the master.

Although improved joint movement may be provided by applying saturation to the joints, when the resulting joint movements differ from the calculated joint movement due to one or more joints reaching their joint ROM limit, saturation of joints may still result in undesirable or counter intuitive master force feedback. To overcome these drawbacks, methods in accordance with the invention include locking (or omitting reliance thereon) of one or more joints when at their respective joint limits within the inverse kinematics calculations such that application of inverse kinematics more intuitive and predictable master force feedback. In one aspect, the methods include locking the one or more joints by modifying an input variable of a Jacobian of the manipulator, the input variable associated with movement of the "locked" joints, such that application of inverse kinematics using the Jacobian causes the joints other than the "locked" joints to arrive at the solution without counting on the contribution from the "locked" joints. It should be noted that movement of the "locked" joints is not inhibited by application of the Jacobian, but rather that the movement of the remaining joints does not rely on the movement of the "locked" joints such that when the "locked" is at its limit, the resulting movement of the remaining joints still arrives at the "right" answer.

In one aspect, the methods and systems in accordance with the invention provide the force feedback to the user that feels "right" (i.e. more intuitive) when a slave range of motion limit is hit. The "right" force feedback is one that optimally guides the user out of the joint limit, that could actually be produced by the slave mechanism, and that in general obeys the laws of physics. Inverse kinematics may be used to achieve that aim. This can be based on a control algorithm for the master manipulator, which produces a force and torque based on the distance between the current master position and the virtual slave position that you feed it. In certain aspects, the system produces a virtual slave position that results in the correct force feedback to the user. Thus, the interaction between the slave inverse kinematics algorithm and the master control algorithm can be utilized so that the end result produces a force feedback that represents the ROM limits to the master in manner that feels "right."

In certain conventional manipulator systems, when a ROM limit is reached, the inverse kinematics converge to some position that is different from the master commanded position. That error between the slave and the master results in a force being felt at the master. However, it may not result in noticeable motion of the slave to some "good" or "bad" position. The position error between the slave and the master is micro-scale, but it may result in macro-scale forces that are felt by the user at the master. Hence, the position error generated by the inverse kinematics algorithm, in accordance with aspect of the invention, is not to control what the user sees, but rather to control what the user feels.

To clarify certain aspects of the invention and separate fundamental principles from implementation details, one may consider the following:

In one example, a mechanism with locked joints can only produce certain force/torque combinations. These combinations are a function of the remaining freedoms of the manipulator, rather than a function of the locked joints. In particular, the allowable force/torque combinations take place in the orthogonal complement of the Jacobian's row space. This means that for a manipulator that is down to five degrees of freedom, the only valid force feedback (for ROM limits) lies in a single-dimensional space.

In one aspect, if you use the Jacobian pseudoinverse to perform the inverse kinematics, the zeroing out the columns of locked joints provides the "right" answer (not zeroing out the joints would result in force feedback that points in entirely the wrong direction producing a non-intuitive master force feedback).

In another aspect, if the Jacobian pseudoinverse is used to perform the inverse kinematics, translation versus rotation must be properly weighed to arrive at the "right" answer (otherwise, the result would be force feedback that points in the wrong direction).

In yet another aspect, if the force feedback for ROM limits relies on a virtual spring between the master and the virtual slave (as our MTM does), then the inverse kinematics should always seek a position/orientation that minimizes the energy in the virtual spring, otherwise, in some cases, the virtual slave may add energy to the spring, in turn violating conservation of energy. This may result in non-intuitive movement of the master. In one example, using the Jacobian pseudoinverse minimizes energy in the spring, assuming that the weighting between translation and rotation matches the strength of virtual springs in the master.

Example methods in accordance with embodiments of the invention include calculating a Jacobian of the manipulator to determine calculated joint movement of the manipulator to achieve a desired state of the end effector and modifying an input variable within the Jacobian relating to movement of a joint of the manipulator when the joint of the manipulator is at or near its respective joint ROM limit. The input variable of the Jacobian may be modified by zeroing out the respective input variable (e.g. the column of the Jacobian associated with movement of the locked joint within the workspace) or by removing the input variables entirely. The latter approach may be useful to apply when the system utilizes the inverse kinematics or at least the Jacobian to effect various other movements, such as null-space movements, that may utilize the range of motion provided by the locked joints. In one aspect, the methods lock certain joints when it is determined that the respective joints are at their associated joint limits, which may be determined in response to saturation of the joint or from output variable associated with states or relative states between joints. In certain embodiments, after certain joints have been locked, the system unlocks the joints in response to a determination that a subsequent movement of the joints in response to achieve a desired tool tip location would move the respective joints away from their joint limits, were the joint included in the inverse kinematics to achieve the desired tool tip location. This may be determined by performing inverse calculations without modified input variable in parallel or may be determined by determining an overlap between a projection of the change in tool tip provided by the locked joints and a change in tool position associated with the goal on the left null-space of the Jacobian having a modified input and determining that the projections overlap on the left null-space. This approach of utilizing a modified Jacobian in which an input variable is modified, by zeroing out the input or removing the variable entirely, is fundamentally different from approaches that modify the joint movements after calculation using inverse kinematics.

In another aspect, the methods include calculated movements that represent to the user when a joint is at a joint limit. For example, when a joint reaches its joint limit and the joint is locked, the user may observe an abrupt or seemingly disproportional movement in the remaining joints. In certain embodiments, the joint movements are calculated by applying a constraint within the inverse kinematics that imposes a relationship between joints or joint movements that mimics load relationships in physical systems, for example, such as in a simple lever or as determined by conservation of energy principles, thereby providing improved movements at the master, when a joint of the manipulator is at its joint ROM limit, that appears more predictable and "natural" to a user.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a surgeon 18 during the procedure. One or more Assistants 20 may also participate in the procedure. The MRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

FIG. 1B diagrammatically illustrates a robotic surgery system 50 (such as MIRE system 10 of FIG. 1A). As discussed above, a Surgeon's Console 52 (such as Surgeon's Console 16 in FIG. 1A) can be used by a surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination of the Electronics Cart 56 and the processor 58, which can be coupled together so as to process the captured images jointly, sequentially, and/or in combinations thereof. One or more separate displays 60 can also be coupled with the processor 58 and/or the Electronics Cart 56 for local and/or remote display of images, such as images of the procedure site, or other related images.

Figure 2:
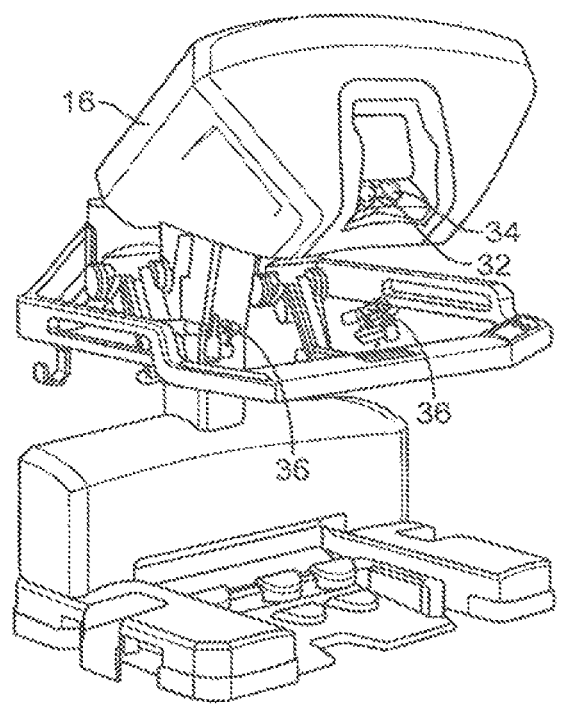
FIG. 2 is a perspective view illustrating a master surgeon console or workstation for inputting surgical procedure commands in the surgical system of FIG. 1, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) so as to provide the surgeon with telepresence, or the perception that the input control devices 36 are integral with the tools 26 so that the surgeon has a strong sense of directly controlling the tools 26. To this end, position, force, and tactile feedback sensors (not shown) may be employed to transmit position, force, and tactile sensations from the tools 26 back to the surgeon's hands through the input control devices 36.

The Surgeon's Console 16 is usually located in the same room as the patient so that the surgeon may directly monitor the procedure, be physically present if necessary, and speak to an Assistant directly rather than over the telephone or other communication medium. However, the surgeon can be located in a different room, a completely different building, or other remote location from the Patient allowing for remote surgical procedures.

Figure 3:
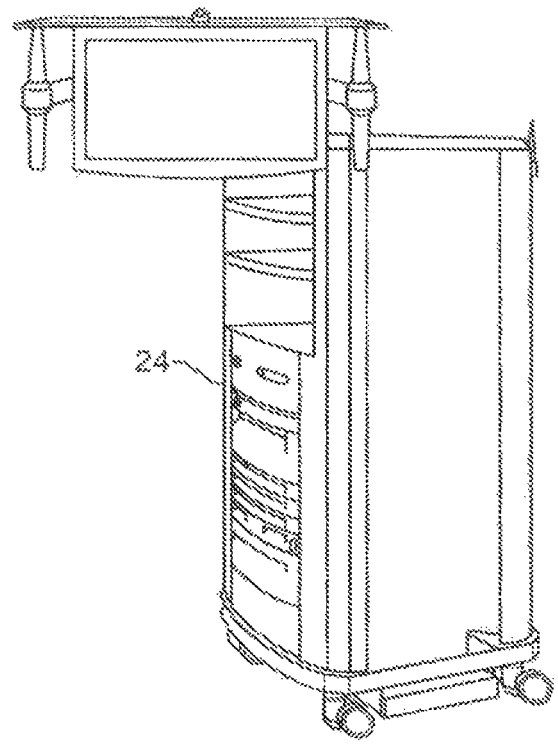
FIG. 3 is a perspective view of the electronics cart of FIG. 1.

FIG. 3 is a perspective view of the Electronics Cart 24. The Electronics Cart 24 can be coupled with the endoscope 28 and can include a processor to process captured images for subsequent display, such as to a surgeon on the Surgeon's Console, or on another suitable display located locally and/or remotely. For example, where a stereoscopic endoscope is used, the Electronics Cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
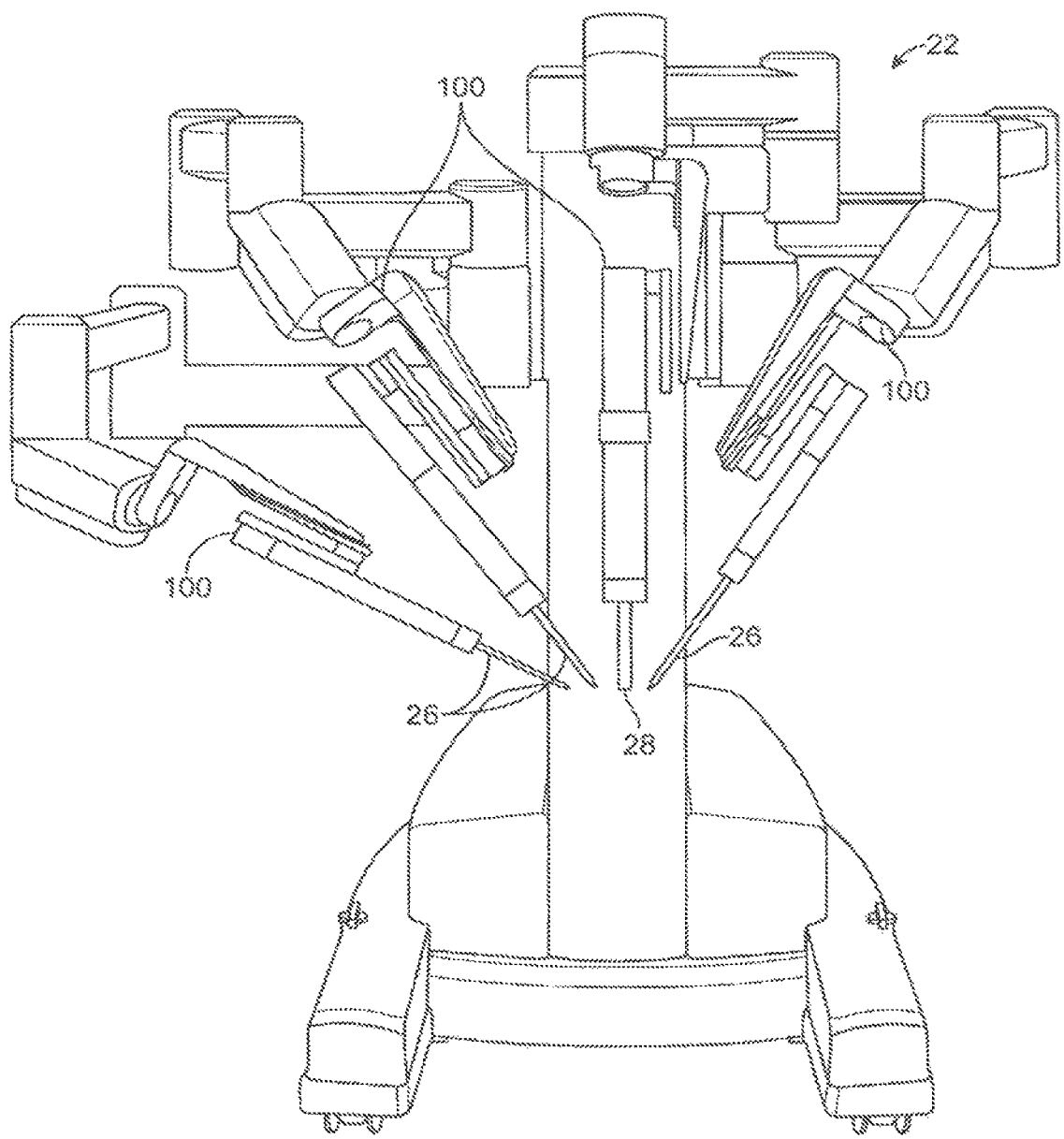
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Example manipulator arms in accordance with many embodiments of the present invention can be understood with reference to FIGS. 5A-13C. As described above, a manipulator arm generally supports a distal instrument or surgical tool and effects movements of the instrument relative to a base. As a number of different instruments having differing end effectors may be sequentially mounted on each manipulator during a surgical procedure (often with the help of a surgical assistant), a distal instrument holder will optionally allow rapid removal and replacement of the mounted instrument or tool. As can be understood with reference to FIG. 4, manipulators are proximally mounted to a base of the patient side cart. In various embodiments, the manipulator arm includes a plurality of linkages and associated joints extending between the base and the distal instrument holder. In certain aspects, an example manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5B:
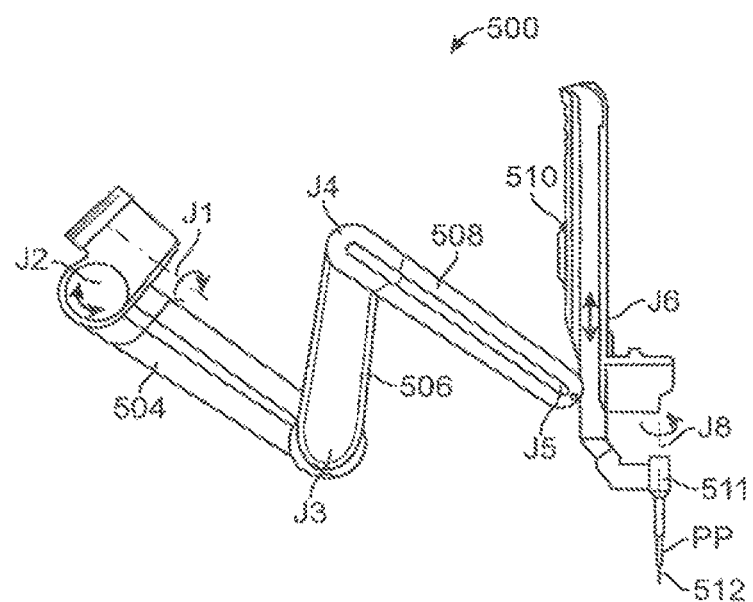

In certain embodiments, such as shown for example in FIG. 5A, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. In various embodiments, distal member 511 is a cannula through which the tool shaft 512 extends, and the instrument holder 510 is a carriage (shown as a brick-like structure that translates on a spar) to which the instrument attaches before extending through the cannula 511 into the body of the patient through the minimally invasive aperture.

Figure 5D:
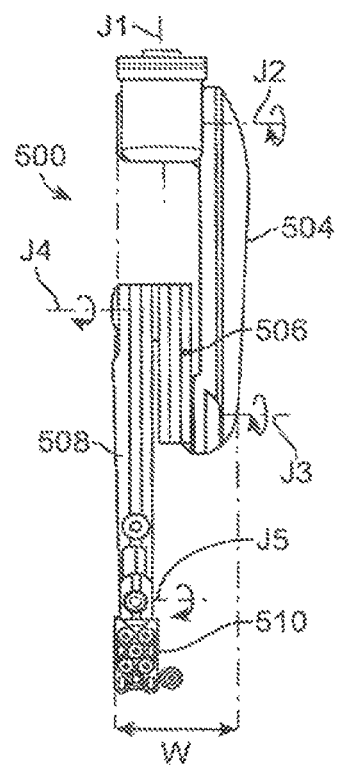
Figure 5C:
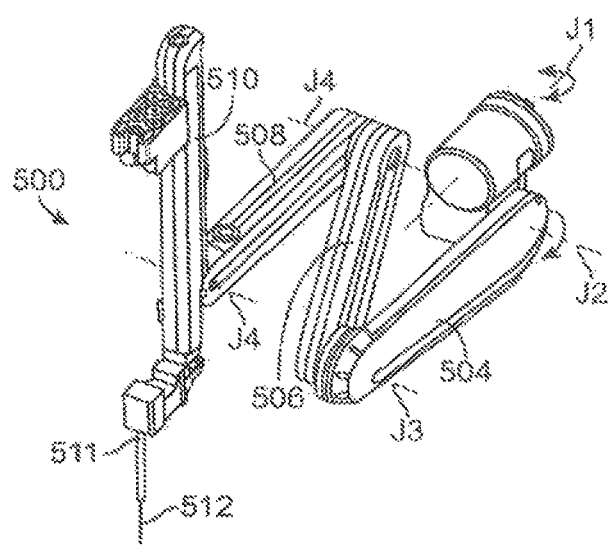

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. In various embodiments, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In various embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint (not shown) near or proximal of the insertion point of the tool tip or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an exemplary manipulator assembly can be appreciated by referring to FIGS. 6A-6C. During a surgical procedure, an exemplary manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In one embodiment, the manipulator arm has a Range of Motion (ROM) of (+/−75 deg) for the outer pitch, and (+/−300 degrees) for the outer yaw joints, respectively. In some embodiments, the ROM may be increased for the outer pitch to provide a ROM larger than (+/−90 deg) in which case the "cone of silence" could be made to disappear entirely, although generally the inner sphere associated with insertion limitations would remain. It is appreciated that various embodiments may be configured to have increased or decreased ROM, that the above noted ROMs are provided for illustrative purposed, and further that the invention is not limited to the ROMs described herein.

FIG. 6C graphically represents the overall range of motion and workspace of the tool tip of the exemplary manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the tool tip may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually moving one or more links of the manipulator to reconfigure the links and joints as desired, which often requires an alternative operating mode and delays the surgical procedure.

In various embodiments, movement of the instrument shaft into or near these conical portions generally occurs when the angle between distal linkages in the manipulator is relatively small. Such configurations can be avoided by reconfiguring the manipulator to increase the angles between linkages (so that the linkages are moved into a more orthogonal position relative to each other). For example, in the configurations shown in FIGS. 6A and 6B, when the angle between the distal most link and the instrument holder (angle a) becomes relatively small movement of the manipulator may become more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well conditioned" so as to maintain dexterity and range of movement. In certain aspects, the present invention allows a user to avoid movement of the instrument shaft near the above described conical portions by simply entering a command to reconfigure the manipulator as desired, even during movement of the end effector in a surgical procedure. This aspect is particularly useful should the manipulator, for whatever reason, become "poorly conditioned."

While the embodiments of the manipulator described above may be utilized in the present invention, some embodiments may include additional joints, which may also be used to improve dexterity and the conditioning of the manipulator arm. For example, an exemplary manipulator may include a revolute joint and/or linkage proximal of joint J1 which can be used to revolve the manipulator arm of FIG. 5A, and its associated cone of silence, about an axis of the revolute joint so as to reduce or eliminate the cone of silence. In another embodiment, the exemplary manipulator may also include a distal pivotal joint that pivots the instrument holder about an axis substantially perpendicular to joint J5, thereby offsetting the tool tip so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator tool tip. The use and advantages of such additional joints can be understood by referring to FIGS. 7A-13C, which illustrate examples of such joints, which may each be used independently of one another or used in combination, in any of the exemplary manipulator arms described herein.

Figure 7A:
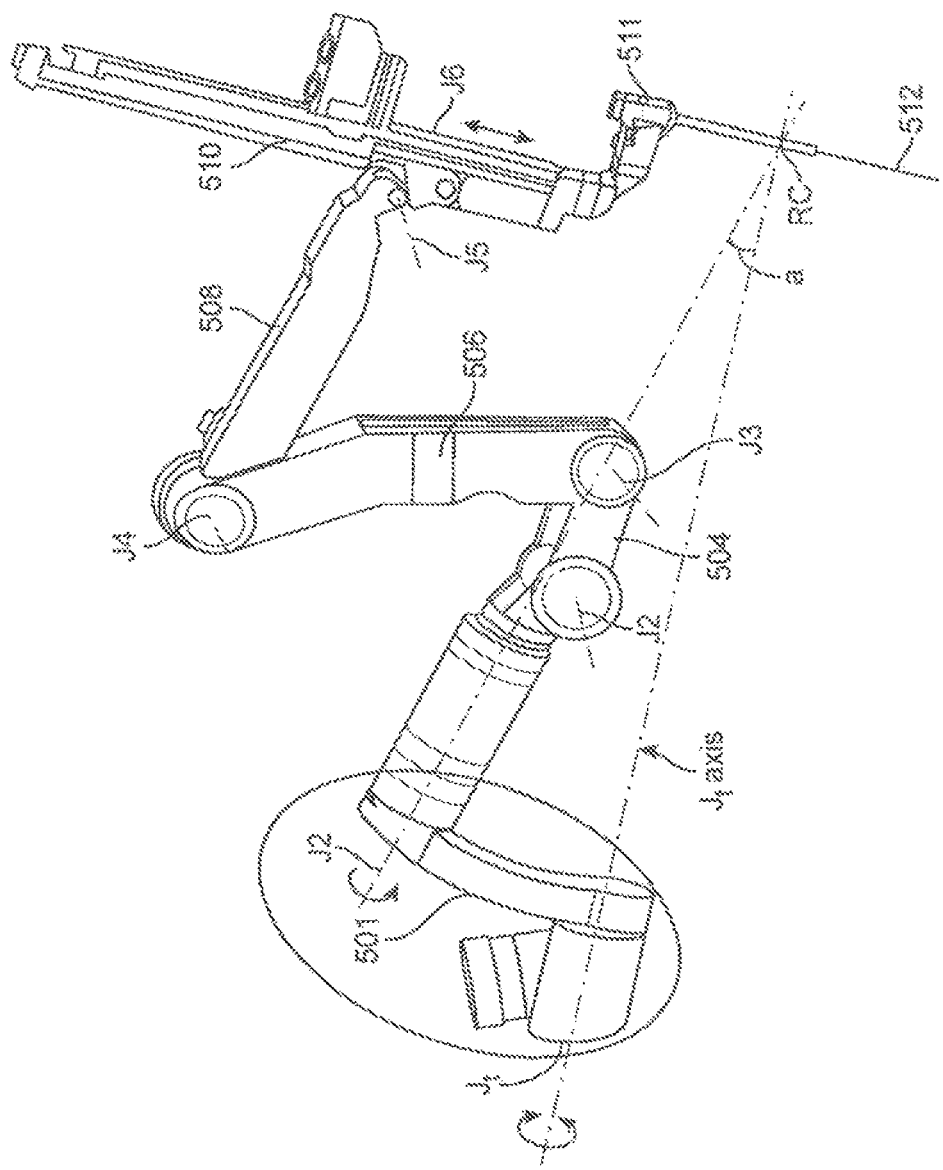
FIG. 7A shows example manipulator arms having a proximal revolute joint that revolves the manipulator arm about an axis of a proximal revolute joint.
Figure 7B:
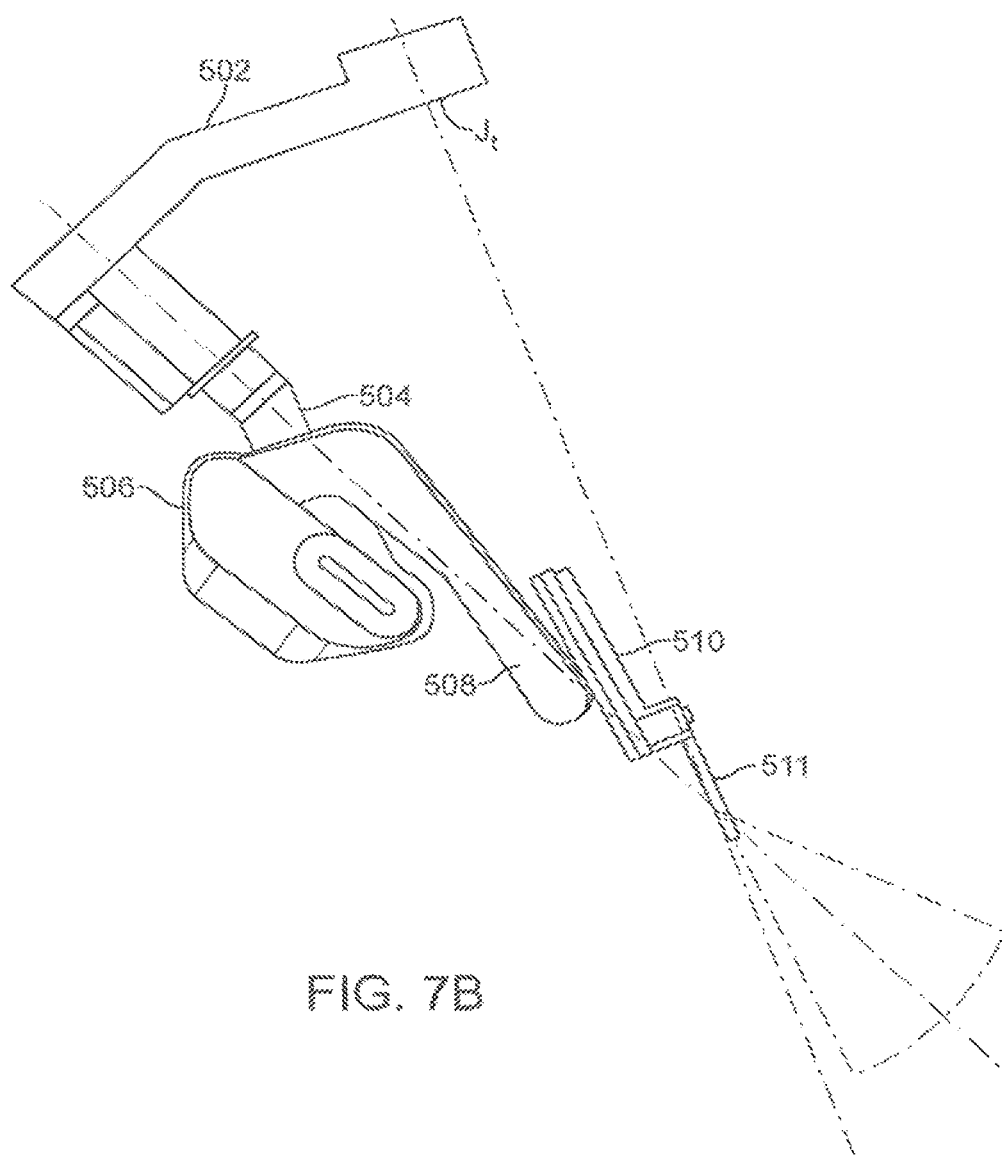
FIG. 7B shows an example manipulator arm and the associated range of motion and cone of silence, the example manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with exemplary manipulator arms—a first joint coupling a proximal portion of the manipulator arm to the base. The first joint is a proximal revolute joint $J_t$ that revolves the manipulator arm about a joint axis of joint $J_t$. The proximal revolute $J_t$ includes a link 501 that offsets joint $J_t$ from the proximal revolute $J_t$ by a pre-determined distance or angle. The link 501 can be a curved linkage, as shown in FIG. 7A, or a linear or angled linkage, as shown in FIG. 7B. The joint axis of the joint $J_t$ may be aligned with the remote center RC or insertion point of the tool tip, as shown in the embodiment of FIG. 7A. In various embodiments, the joint axis of joint $J_t$ passes through the remote center, as does each other revolute joint axis in the manipulator arm, to prevent motion at the body wall and can therefore be moved during surgery. The axis of joint $J_t$ is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy. In certain aspects, the proximal revolute $J_t$ is used solely to change the mounting angle of the manipulator with respect to the floor. This angle is important in order to 1) avoid collisions with external patient anatomy and 2) reach anatomy inside the body. In various embodiments, the angle a between the proximal link of the manipulator attached to the proximal revolute joint $J_t$ and the axis of the proximal revolute is about 15 degrees.

FIG. 7B illustrates the relationship of the proximal revolute joint $J_t$ and its associated joint axis and the cone of silence in an exemplary manipulator arm. The joint axis of the proximal revolute joint $J_t$ may pass through the cone of silence or may be completely outside of the cone of silence. By revolving the manipulator arm about the axis of the proximal revolute $J_t$, the cone of silence can be reduced (in an embodiment where the joint $J_t$ axis passes through the cone of silence), or can be effectively eliminated (in an embodiment where the proximal revolute joint axis extends completely outside the cone of silence). The distance and angle of the link 501 determines the position of the joint $J_t$ axis relative to the cone of silence.

Figure 8:
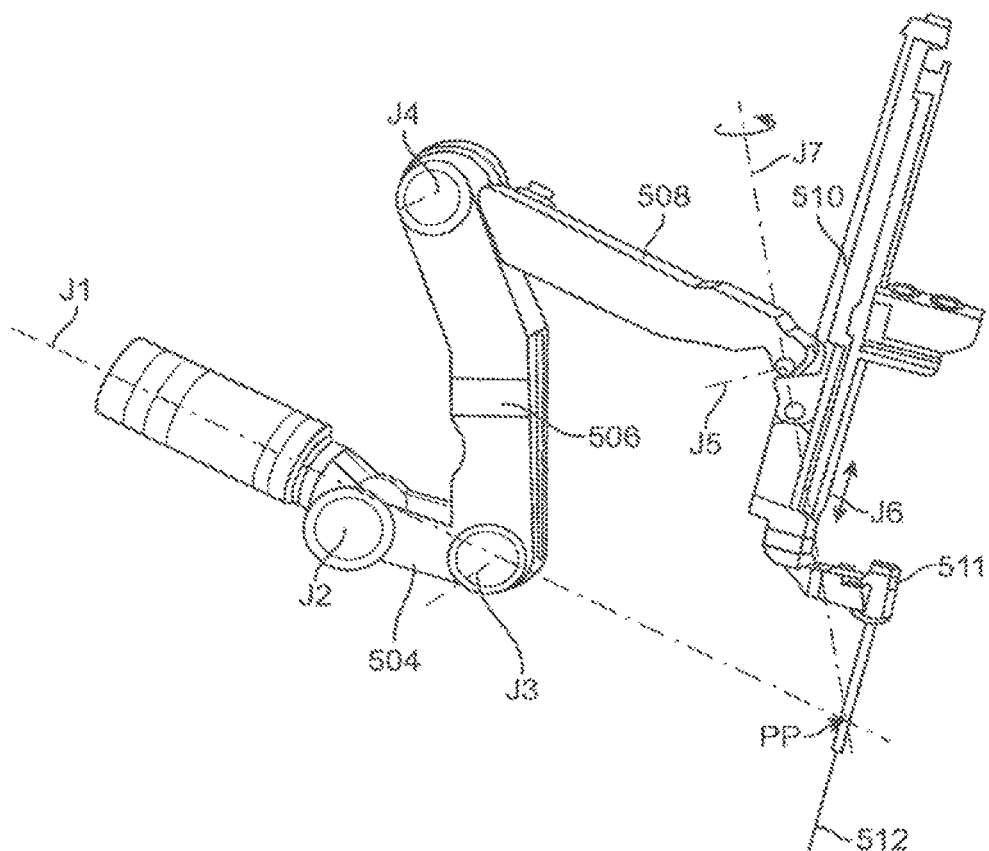
FIG. 8 shows an example manipulator arm having a revolute joint near the distal instrument holder.
Figure 9:
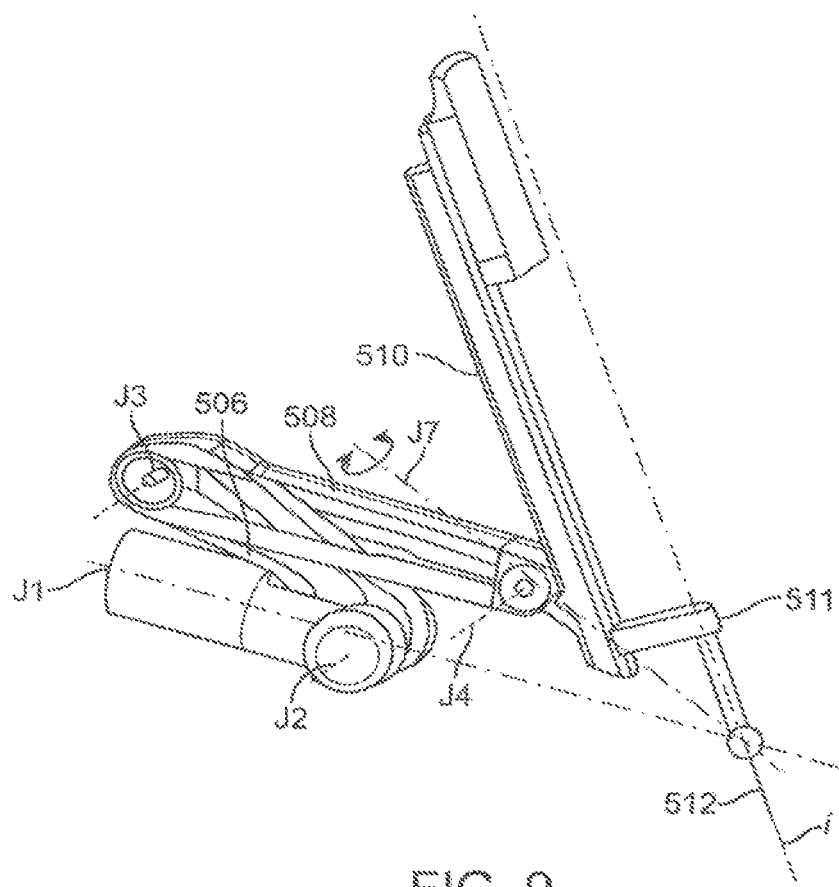
FIG. 9 shows an example manipulator arm having a revolute joint near the distal instrument holder that revolves or twists the instrument holder about the joint axis.
Figure 10A:
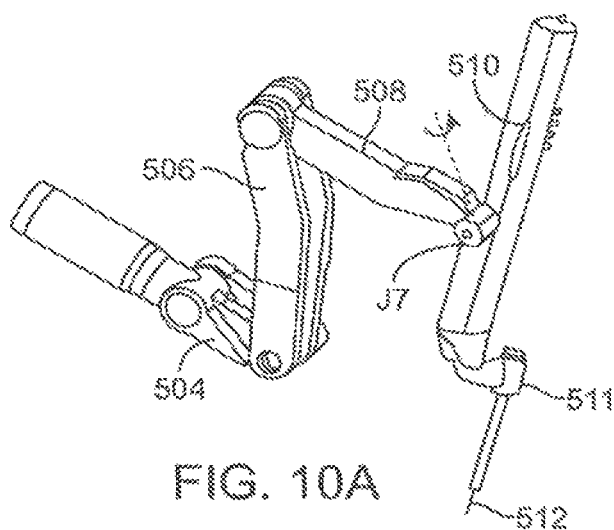
FIGS. 10A-10C show sequential views of an example manipulator arm having a revolute joint near a distal instrument holder as the joint is moved throughout its range of joint movement.
Figure 10B:
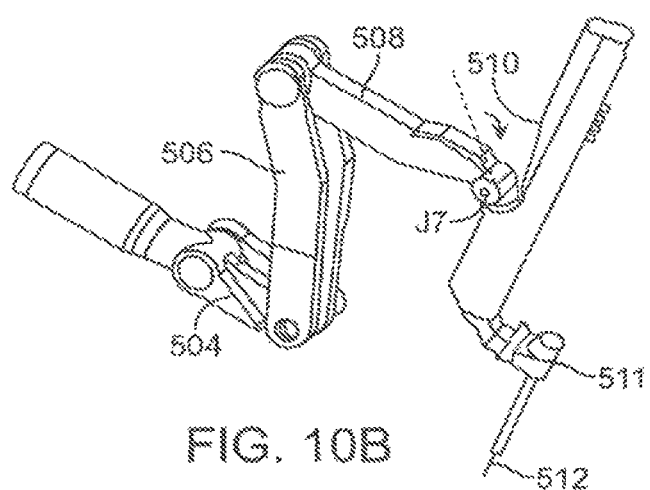
Figure 10C:
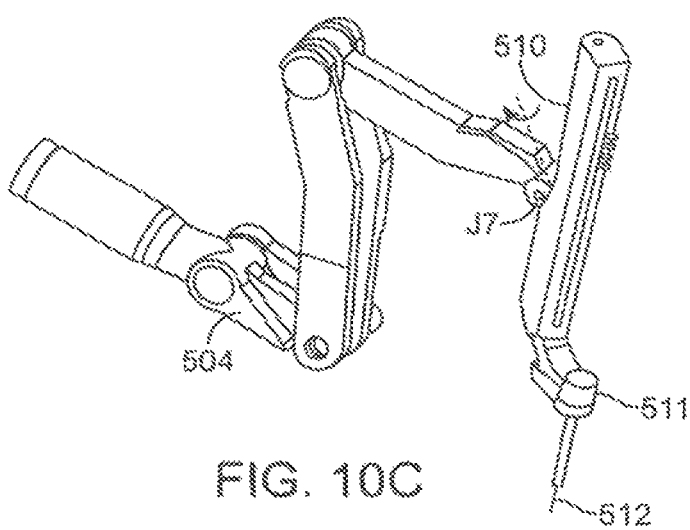

FIG. 8 illustrates another type of redundant joint for use with exemplary manipulator arms, a distal revolute joint J7 coupling the instrument holder 510 to a distal link of the manipulator arm 508. The distal revolute joint J7 allows the system to twist the instrument holder 510 about the joint axis, which in various embodiments passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint J7 has the ability to move the insertion axis closer to the yaw axis, it is able to increase arm pitch back range of motion. The relationship between the axis of the distal revolute joint J7, the yaw axis of J1 and the insertion axis of tool tip is shown in FIG. 9. FIGS. 10A-10C show the sequential movement of the J7 and how it shifts the insertion axis of tool tip from side to side.

Figure 11A:
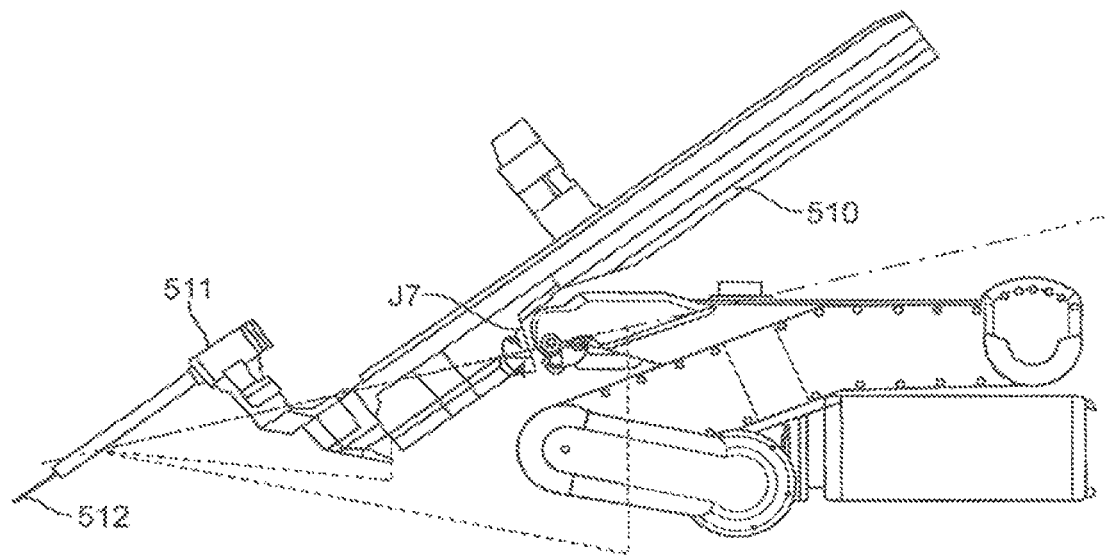
FIGS. 11A-11B show the revolved profile of an example manipulator arm having a distal revolute joint when the angular displacement of the joint is 0° versus an angular displacement of 90°, respectively.
Figure 11B:
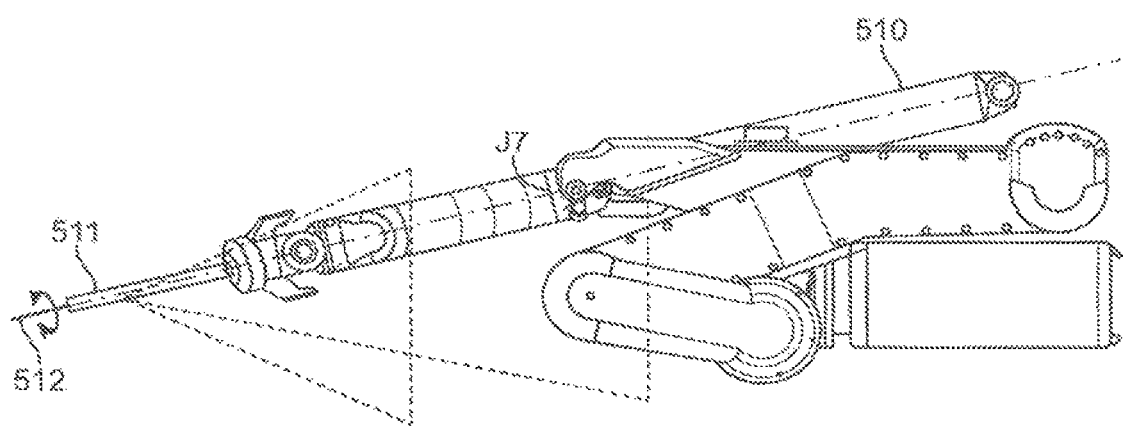

Another advantage of the distal revolute joint J7 is that it may reduce the patient clearance cone, which is the swept volume of the distal portion of the manipulator arm proximal of the insertion point that should clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint J7 in accordance with the present invention may provide additional clearance while maintaining the remote center location or the position of the end effector as desired.

Figure 12:
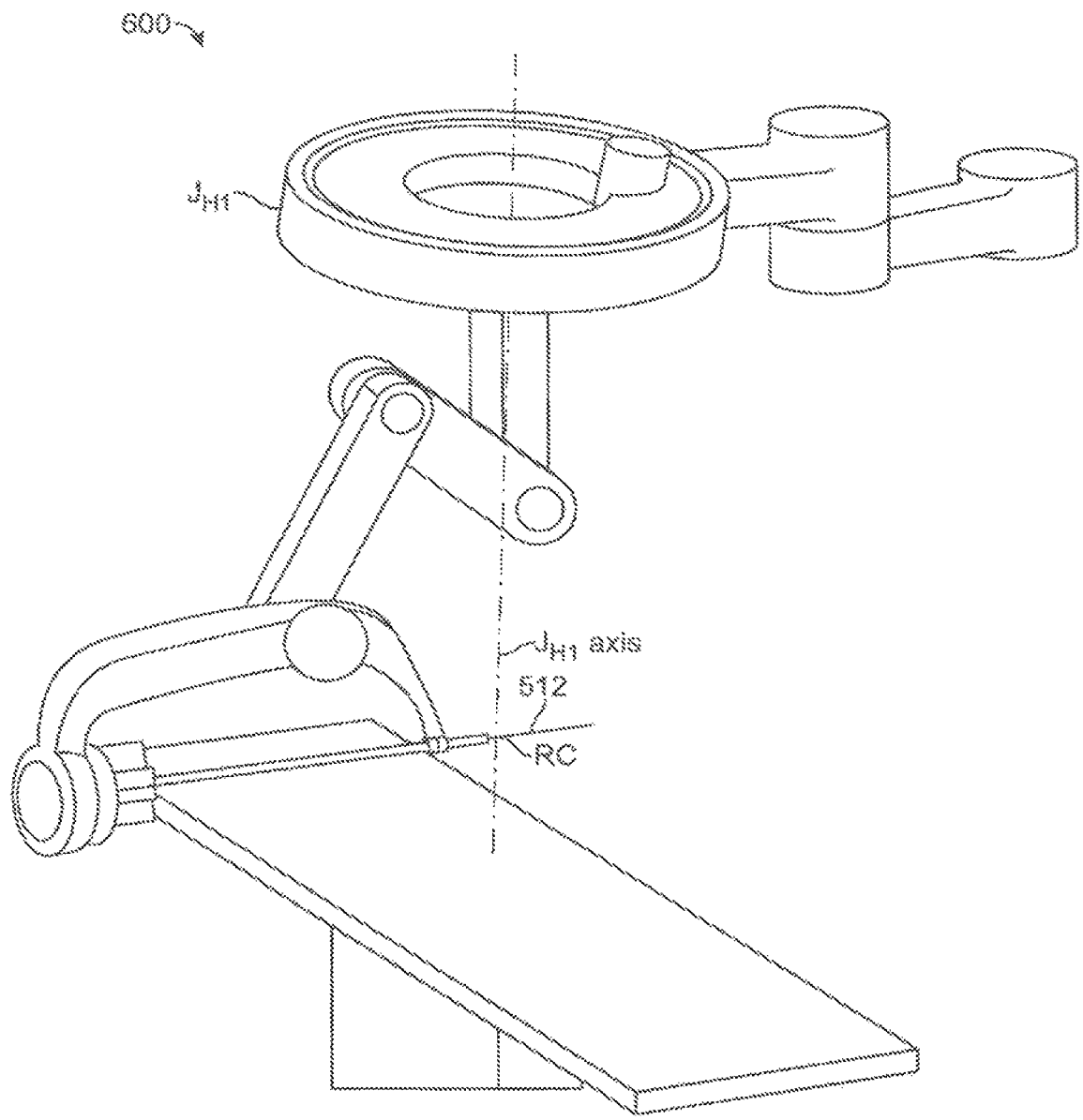
FIG. 12 show example manipulator arms having a proximal joint that translates a proximal joint supporting the manipulator arm about a path of the joint.
Figure 13A:
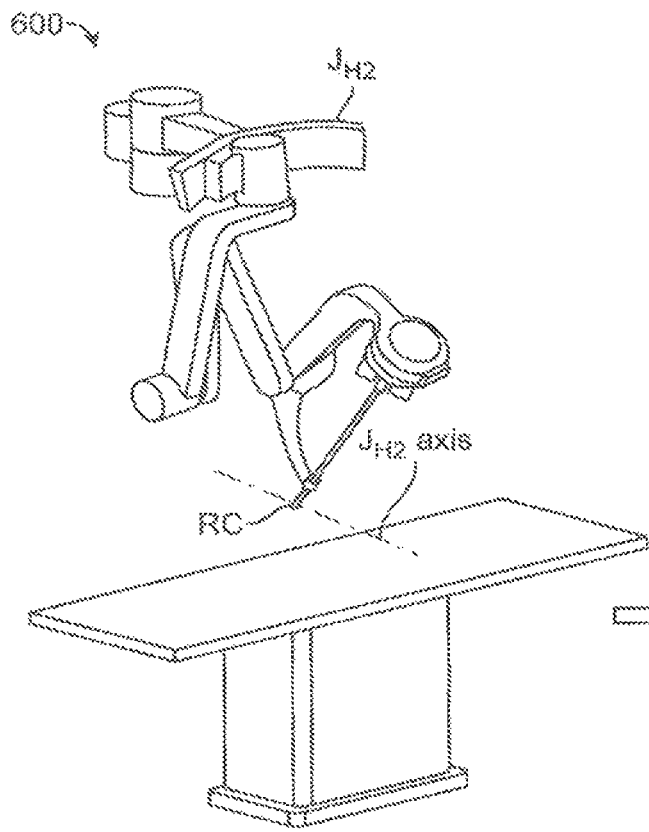
FIGS. 13A-13C show example manipulator arms having a proximal joint that translates a proximal joint supporting the manipulator arm about a path of the joint.
Figure 13B:
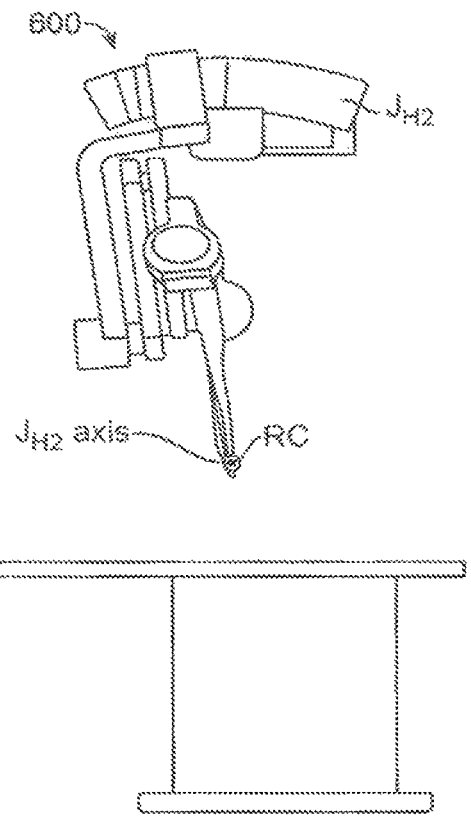
Figure 13C:
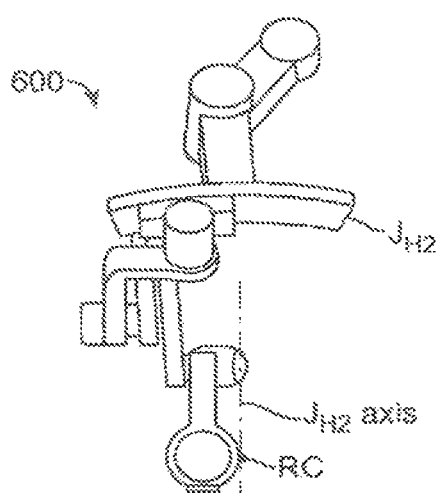

FIG. 12-13C illustrate another type of redundant joint for use with exemplary manipulator arms, a proximal joint that translates or revolves the manipulator arm about an axis. In various embodiments, this proximal translatable joint translates a proximal joint of the manipulator, such as joint J1 or $J_t$, along a path so as to reduce or eliminate the cone of silence by shifting or rotating the range of motion of the manipulator arm to provide for better conditioning and improved maneuverability of the manipulator arm. The translatable joint may include a circular path, such as shown in joint $J_{H1}$ in FIG. 12, or may include a semi-circular or arcuate path, such as shown in FIGS. 13A-13C. Generally, the joint revolves the manipulator arm about an axis of the translatable joint that intersects with the remote center RC about which the shaft of the tool 512 extending through cannula 511 pivots. In the embodiment shown in FIG. 12, this axis of $J_{H1}$ is a vertical axis, whereas in the embodiment shown in FIGS. 13A-13C the axis of $J_{H2}$ is horizontal.

In certain embodiments, the manipulator arm 500 may include any or all of the a proximal or distal revolute joint, a proximal translatable joint and a parallelogram configuration of the distal linkages. Use of any or all of these features provide additional redundant degrees of freedom and facilitate reconfiguration in accordance with the present invention so as to provide for a better "conditioned" manipulator assembly by increasing the angles between linkages thereby improving the dexterity and motion of the manipulator. The increased flexibility of this exemplary manipulator can also be used to optimize the kinematics of the manipulator linkage so as to avoid joint limits, singularities, and the like.

In some embodiments, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

In an exemplary embodiment, the system includes a controller in which a commanded position and velocity of a feature in the work-space, denoted here as its Cartesian-coordinate space (referred to herein as Cartesian-space), are inputs. The feature may be any feature on the manipulator or off the manipulator which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudoinverse of the Jacobian ($J^\#$). The resulting joint-space commanded velocity is then integrated to produce joint-space commanded position (q). These relationships are listed below:

$$dx/dt = dx_{des}/dt + k\Delta x \quad \text{(i)}$$

$$dq/dt = J^\# dx/dt \quad \text{(ii)}$$

$$q_i = q_{i-1} + dq/dt \Delta t \quad \text{(iii)}$$

The pseudoinverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional three joint axes for the three degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory or path of joint positions which also produces no instantaneous movement of the tool tip and/or location of the remote center. Calculated null-space velocities can be incorporated or injected into the control system of the manipulator to achieve a desired movement of the manipulator arm by changing above equation (ii) to the following:

$$dq/dt = dq_{perp}/dt + dq_{null}/dt$$

$$dq_{perp}/dt = J^\# dx/dt$$

$$dq_{null}/dt = (1 - J^\# J)z = V_n V_n^T z = V_n \alpha$$

I. "Locking" of Joints at Joint Range of Motion Limits

Figure 14:
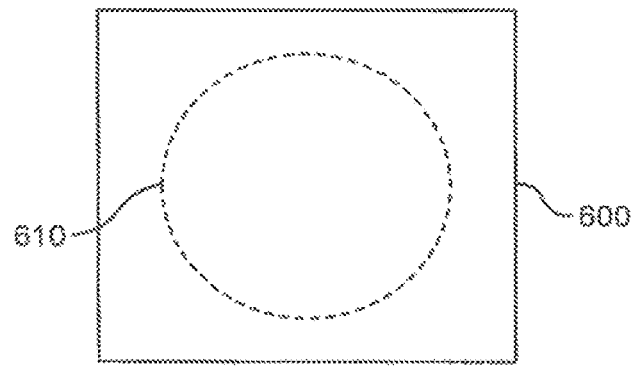
FIG. 14 graphically represents a join range of motion of an instrument wrist of the manipulator and an imposed joint constraint.

FIG. 14 graphically illustrates a range of movement provided by an instrument wrist of an example manipulator arm, the wrist having a pitch and yaw of 60 degrees in each direction, such that the wrist joints have a square range of motion. In this example, when the wrist is backed into a corner region of its range of motion, movement becomes impaired since turning of the wrist becomes difficult, if not impossible, in the extreme corner regions, which may result in movement that fails to achieve the desired tool tip position or other impaired joint movements. For each goal position, there is a maximum joint motion associated with a given joint (e.g. a joint can only move so far). To avoid this problem, the system software can enforce an artificial joint limit 610, a Cartesian-based range of motion limit, in which the wrist movement is confined.

Figure 15:
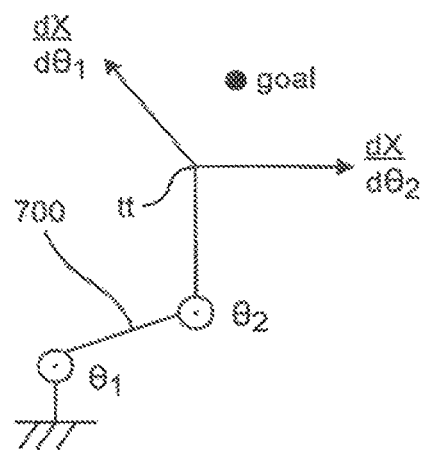
FIG. 15 graphically depicts joint movement of first and second joints of a manipulator calculated by inverse kinematics to provide a desired goal tool tip position.

Although saturation may be applied to one or more joints to avoid undesirable shifts when joint limits become coupled, this approach also has drawbacks. For example, since saturation is applied after performing inverse kinematics on the joints, if one joint is hitting its actual joint limit, then the inverse kinematics that are being saturated are not accurate, such that even if saturation were applied, the resulting movement of the tool tip may be away from the goal. This aspect is illustrated in FIG. 15, which depicts a manipulator configuration 700 having a first joint θ1, a second joint θ2 and distal tool tip tt. The arrows dX/dθ1 and dX/dθ2 represent calculated movement of the tool tip attributable to the first and second joints, respectively, calculated using inverse kinematics. In particular, each corresponds to the columns of the Jacobian matrix, shown below, of the inverse kinematics of the manipulator. The goal position of the tool tip tt used in the inverse kinematics calculations is also shown. Although according to the inverse kinematics, equal motion of the first joint θ1 and second joint θ2 would move the tool tip toward the goal, if θ2 is at its joint limit, then only joint θ1 moves such that the resulting motion of the tool tip tt is perpendicular to the goal. Even if saturation is applied, since the underlying inverse kinematics do not accurately represent the resulting joint movements, additional limits may have to be enforce to inhibit movement of the joints near their respective limits, thereby unnecessarily reducing the joint ROM of each joint.

$$dx = \begin{bmatrix} -1 & 1 \\ 1 & 0 \end{bmatrix} d\theta$$

$$dx = \begin{bmatrix} 1 \\ 1 \end{bmatrix} \Rightarrow d\theta = \begin{bmatrix} 1 \\ 2 \end{bmatrix}$$

saturate $d\theta$:

$$d\theta = \begin{bmatrix} 1 \\ 0 \end{bmatrix} \Rightarrow d\theta = \begin{bmatrix} -1 \\ 1 \end{bmatrix}$$

Therefore, to avoid calculation of a joint movement for a joint that beyond its joint ROM limit, such joints may be "locked" within the inverse kinematics used in calculation of joint movements for a desired end effector position. It is desirable to "lock" such joints within the inverse kinematics calculations since the complexities associated with additional calculations relating to corrective, compensating or reconfiguration movements can be avoided. In accordance with certain aspects of the invention, joints that are at their respective joint ROM limits can be locked by modifying an input of a Jacobian matrix within the inverse kinematics, the input corresponding to movement of the joint within the workspace. It is appreciated that "locking" of a certain joint does not refer to a mechanical locking or inhibiting of joint movement but rather a modification of the inverse kinematics calculations that results in no movement of the locked joint such that the remaining joints do not rely on movement of the "locked" joints when. For example, as shown in the following equation, by zeroing the variable of the column of the Jacobian corresponding to movement of the joint at its limit, the calculated joint movement of the remaining joints performed in the inverse kinematics accounts for the inability of the joint at its limit to move so that the resulting calculated joint states provide the desired state of the end effector. An example of this operation is shown in the following equations:

$$dx = \begin{bmatrix} -1 & 0 \\ 1 & 0 \end{bmatrix} d\theta$$

$$dx = \begin{bmatrix} 1 \\ 1 \end{bmatrix} \Rightarrow d\theta = \begin{bmatrix} 0 \\ 0 \end{bmatrix}$$

In another aspect, the input of the Jacobian may be modified by removing the column associated with movement of the locked joint entirely. This approach may be advantageous in systems configured to utilize the Jacobian for calculation of various other movements, such as a movement within the null-space or various other types of movements, that may calculated a corresponding movement of the joint that is desired to be locked.

A. Weighting Position Versus Rotation

In one aspect, methods weight certain joints or types of joint movements, such as translation and rotation, when locking one or more joints of the manipulator as described herein. When a joint locks, the Jacobian becomes singular. This may result in an abrupt shift between types of joint movements, which may produce movements that are undesirable, impaired, or at least appear counter-intuitive to a user. By weighting certain joints or certain types of joint movements, the resulting movement may appear smoother. This result can be understood further by considering how the joints movements are calculated within inverse kinematics in certain manipulator systems. The pseudoinverse of the Jacobian results in joint movement (θ) that yields a minimum sum-squared-error (SSE) to the goal in Cartesian-coordinates, such as in the following equation:

$$dx = Jd\theta$$

In such an SSE, however, joint movements associated with rotation and position of the joint are combined. For various reasons, it may be desirable to weight position or rotation of the joints differently. In certain methods, this weighting is achieved by applying a diagonal weighting matrix that varies the weight between position and rotation within the inverse kinematics calculation. For example, the pseudoinvert (WJ) produces the minimum SSE to the weighting matrix (Wdx), such as in the following equation:

$$(Wdx)=(WJ)d\theta$$

B. Locking and Unlocking of Joints

1. Locking of Joints at Joint ROM Limits

In one aspect, the system considers one or more joints of a particular manipulator as "locked," when the one or more joints is at its respective joint ROM limit. In certain embodiments, when the change in joint position (d θ) becomes saturated, the joint is at its limit and the joint is "locked."

2. Unlocking of Locked Joints

Once one or more joints of the manipulator are locked, there are various approaches to determine when some or all of the locked joints should be unlocked and utilized in subsequent joint movements. In some embodiments, the joint may remain locked for a predetermined duration, such as for one or more subsequent servo cycles. In some embodiments, the "locked" joints are unlocked when movement of the joint, if allowed to move, to effect a desired end effector state, would move the joint away from its respective joint ROM limit. This may be accomplished by performing a calculation in parallel using a Jacobian matrix without modification of the input relating to the locked joint. However, this approach may become overly complex, particularly when multiple joints are "locked" such that various combinations of locked and unlocked joints would be possible, which may necessitate a separate inverse kinematics calculation for each combination.

Figure 16:
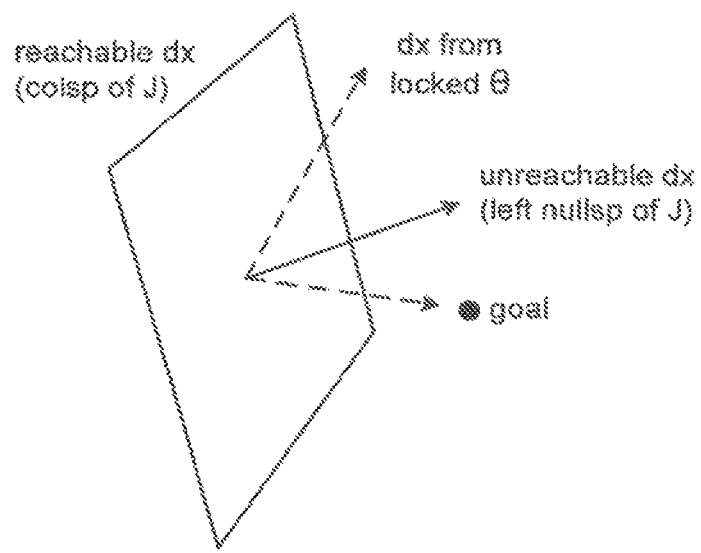
FIG. 16 graphically depicts the change in tool tip position associated with a locked joint relative a change in position associated with the goal tool tip position in the workspace.

In one aspect, the "locked" joints are unlocked when movement of the joint provides a change in position of the tool tip that is toward the goal. One approach to achieve this function is illustrated in FIG. 16. The column space of the Jacobian represents the reachable dx, while the left-nullspace of the Jacobian represents the dx that is unreachable. When a joint is locked, the dx associated with the locked joint is no longer accessible. By projecting the dx from the locked joint onto the left-nullspace of the Jacobian it can be determined whether movement of the locked joint can provide any change in position of the tool tip that would otherwise remain unreachable. This is likely only relevant, however, if the change in position or dx to effect the desired goal position of the tool tip is within this unreachable dx. Therefore, it can be determined whether the locked joint can provide any change in joint position to move the tool tip toward the desired goal location by projecting each of the dx from the locked joint and the desired goal dx onto the left-nullspace. If each ray has a component on the left-nullspace, then the dx associated with the locked joint can provide movement toward the goal dx. In response to this determination, the system unlocks the locked joint. When multiple joints are locked, this approach may be utilized with respect to each locked joint such that only the select joints meeting this criteria are unlocked. This approach arrives at the minimum SSE in Cartesian-coordinates. This approach is demonstrated by the following equation, in which U is the orthonormal basis for projecting onto the left-nullspace, such as in the following equation:

$$JV = USV^TV = US$$

Figure 17:
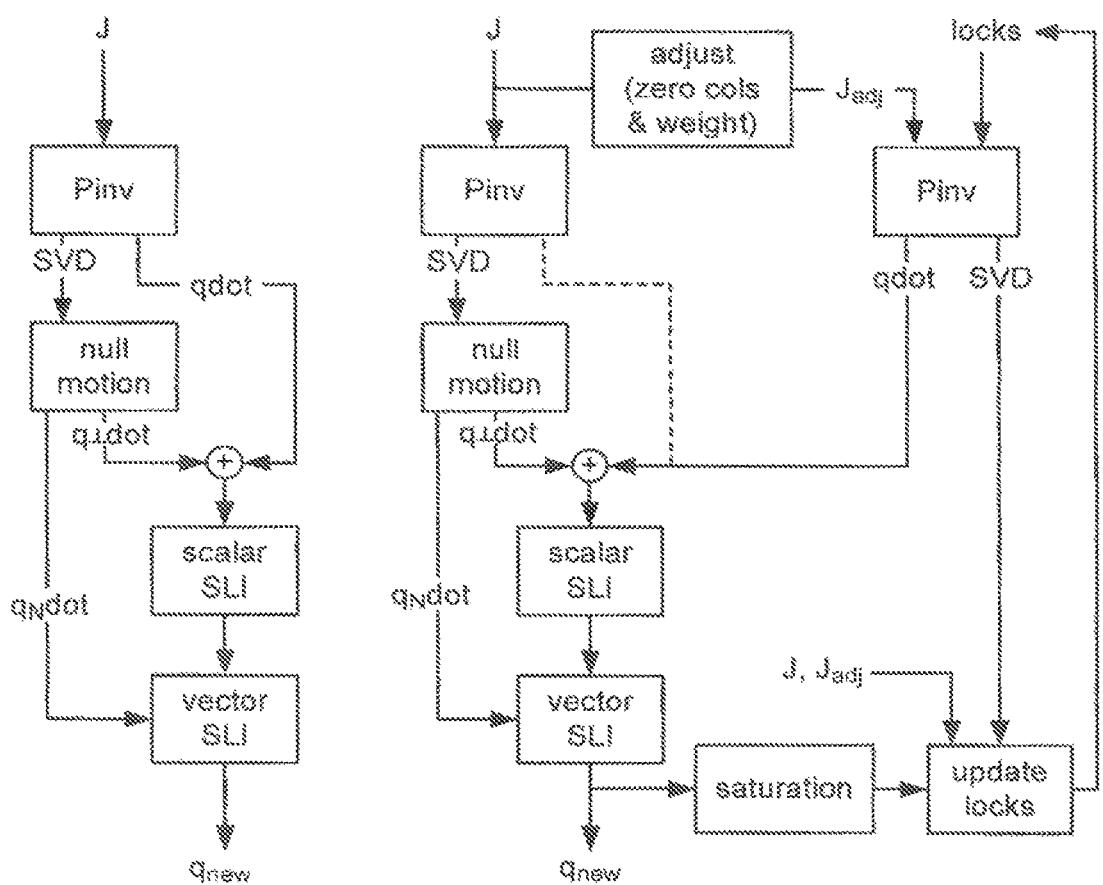
FIG. 17 graphically depicts an example code implementation in accordance with embodiments of the invention.

FIG. 17 illustrates an example code implementation to perform the locking and unlocking of certain joints of a manipulator, in accordance with the embodiments described above. As schematically illustrated, the manipulator system is controlled such that the features relating to null motion does not utilize joint movements of locked joints. Movements provided by null-motion of the remaining unlocked joints, however, may still be effected.

II. Controlling Joint Behavior at Joint Limits

In another aspect, joint movements are calculated such that movement of joints provide movements at or near their respective limits appears consistent with joint movements at limits within physical systems. Given the number of degrees of freedom and redundancies in a highly configurable manipulator, movement of a joint at its limit may result in movement of other joints such that the behavior of the joints at its limit may appear counter-intuitive to a user. To reduce these perceived inconsistencies in movement, there are several approaches in which joint movements are calculated to provide improved and more intuitive movement of the manipulator arm, particularly when one or more joints are at their respective limits.

In one approach, the system determines the closest allowable position of the locked joint to the goal location in the Cartesian-coordinate system. This may be achieved by use of a position priority calculation, weighting between position and orientation; by solving inverse kinematics without limits, then saturating the joints; and/or by calculating joints movements so that a wrist of the manipulator achieves a desired orientation of the distal tool tip, while the manipulator arm proximal the wrist achieves the tool tip position.

Figure 18A:
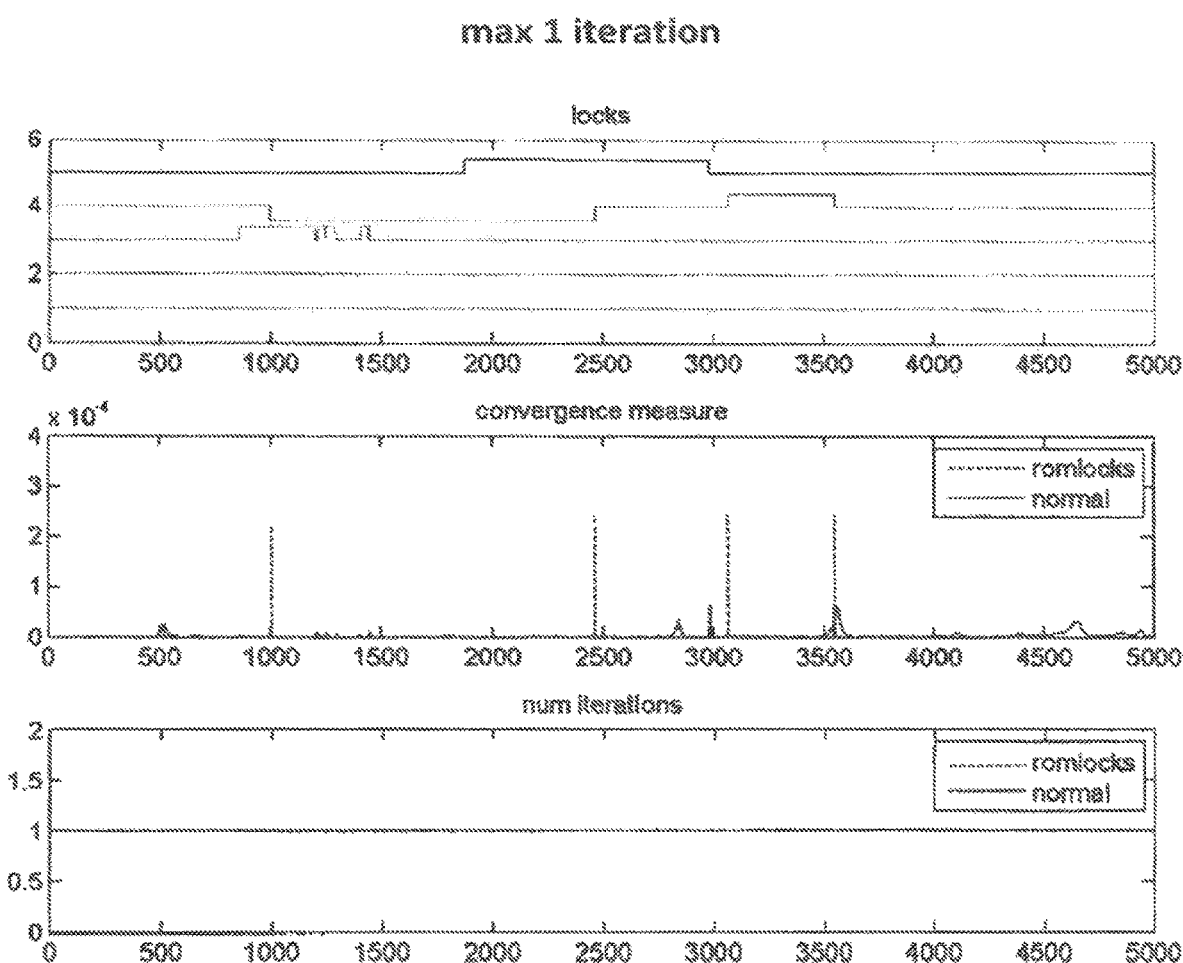
FIGS. 18A-18B depict an example of timing transitions between locked and unlocked joint states in iterations of inverse kinematics calculations used to control joint movements.
Figure 18B:
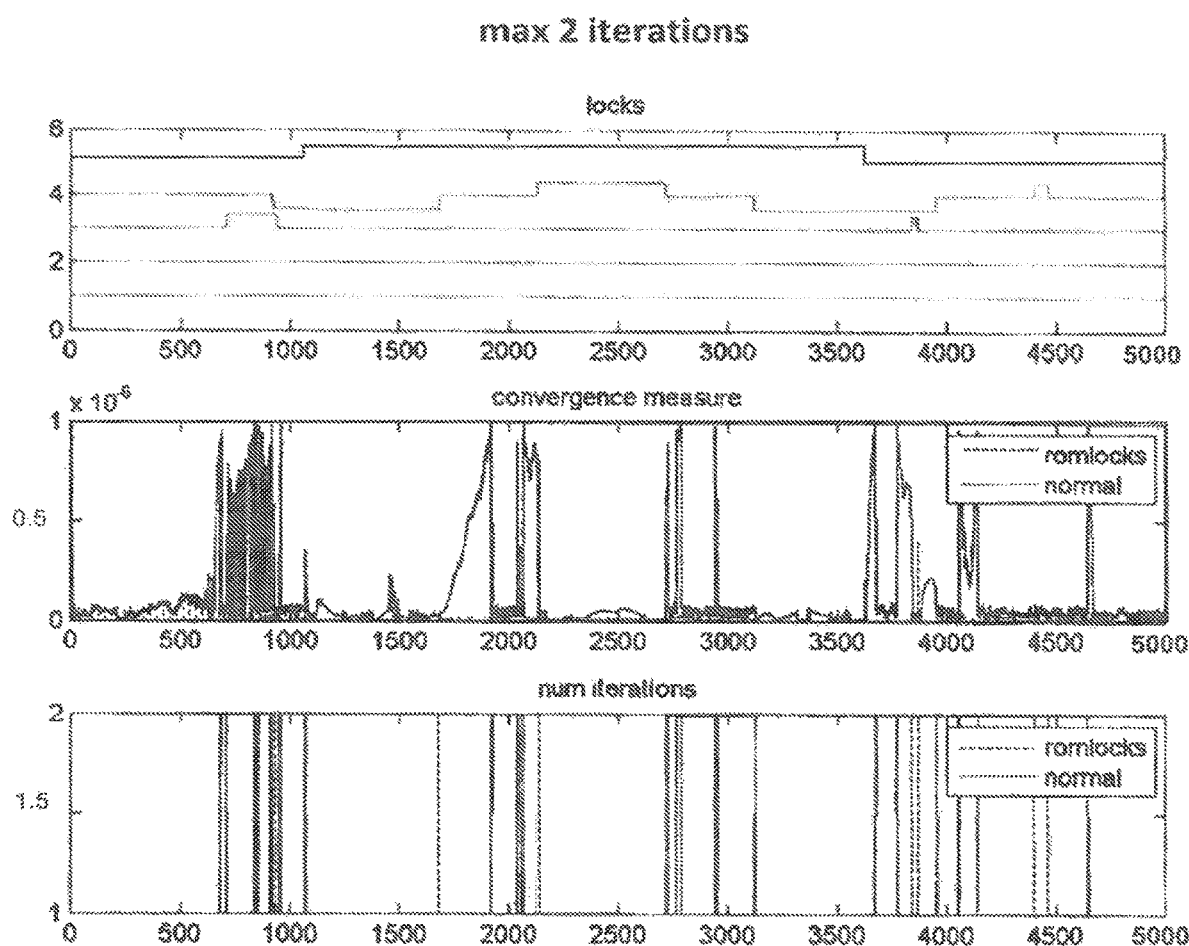
Figure 19:
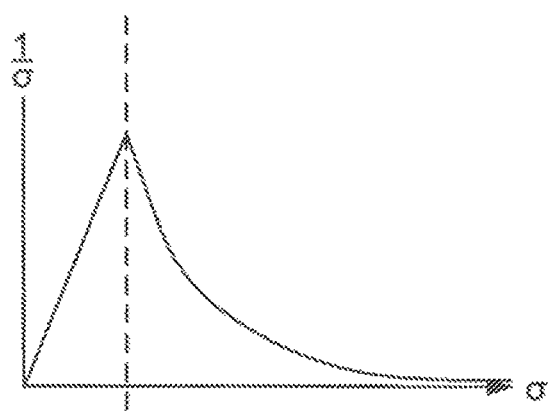
FIG. 19 illustrate a smooth transition in a singularity of the Jacobian matrix formed when a joint is locked.

Another aspect associated with locking or unlocking of one or more joints is determining when the joints transition between locked and unlocked states. Depending on the joint states and configuration and the timing of the transition, the resulting joint movements may result in counter-intuitive movements of certain joints. FIGS. 18A-18B illustrate examples of the Jacob iterations used in a singular value decomposition for use in determining the transition of locking and unlocking joints. Unlocking of one or more joints may also be dependent on a given configuration or state of various other joints. For example, unlocking of one or more joints may be based on whether the joint movement that would result from the unlocked joint would result in an increase in tip roll, exceeding certain velocities in one or more joints, or various other conditions. In some embodiments, joint movements are calculated to move along a surface in the joint space so as to create a smoother transition when certain joints are locked and unlocked creating a singularity in the Jacobian matrix. FIG. 19 illustrates an example of a smooth transition at a singularity which would be desirable to achieve by the methods described herein.

A. Calculated Joint Movements to Emulate Physical System Behaviors at Joint Limits Although "locking" certain joints at their respective limits allows increased capability and range-of-motion while avoiding undesirable movement of the tool tip away from the desired goal location, "locking" of joints may still result in master force feedback that may appear unpredictable, disproportional or counter-intuitive. Since such constraints often involve a combination of translation and rotation, which can be confusing to the user, it is useful to express these limits and constraints to the user as intuitively as possible. In certain embodiments, methods include calculated movements that express the joint ROM limits to the user by mimicking behavior in physical systems. In contrast, to conventional haptic systems that utilized an additional movement displayed to the user, such as a vibration or an additional movement in response, the methods described herein modify existing calculated joint movements so that the joint movements that occur appear more consistent with what would be expected in a physical system. Various approaches to achieve this are described in further detail below.

In many manipulator systems described herein, the gains that convert position error to force, and orientation error to torque, are independent. Since physical systems enforce relationships between force and torque, expressing the ROM limit constraints according to the same rules that apply to physical systems would convey the ROM limits to the user in a more intuitive manner. In one aspect, the minimum SSE solution to inverse kinematics can be used to fulfill this goal of emulating a physical system. Under certain assumptions, the minimum SSE solution to inverse kinematics is the only algorithm that always obeys conservation of energy (e.g. does not energy to the virtual spring between master and virtual slave).

Representing the joint ROM limits to the user in a more intuitive manner improves the manipulator movement and response to commanded movements as perceived by the user. In one example manipulator having an endoscopic camera, while working on camera control, when pushing the masters forward a small amount, the user would feel a relatively large torque on the handlebar in return (due to one joint hitting its ROM limit during coupled joint movements). While this dramatic shift in both magnitude and type of joint movement is kinematically correct since there is a significant coupling between position and orientation in the ROM constraints (especially for a 30° scope), this result may seem counter-intuitive to a user. For example, a user would not expect to give a little force in and receive a big torque out in return. More specifically, a user would generally not expect to put in a small force over a small distance and get out a big torque over a big angular distance as this would seem contrary to conservation of energy that would hold true in a purely physical system. This issue arises since in many software controlled manipulator systems, force and torque are handled independently. For example, the masters multiply position error times one gain to obtain force, and multiply orientation error times another gain to obtain torque.

In one aspect, methods of control are applied that emulate the constraints between force and torque corresponding to load relationships that exist in real-world physical systems. In particular, this method can be implemented using the approach previously described, by minimizing SSE between the goal and the virtual slave, along with the existing algorithm on the masters and giving feedback forces/torques proportional to the error between the master (e.g. Master Tool Manipulator or "MTM") and the virtual slave. For convenience this entire algorithm is referred to as "Minimum SSE inverse kinematics".

There are various approaches that can be taken in regard to this analysis. In the first approach, forces and torques on a single-DOF lever are considered, and certain constraints that the algorithm obeys are derived. In the second approach, an energy-based relationship can be applied and generalized with respect to many DOFs without requiring knowledge of the specific kinematics of the mechanism.

In the first approach, the constraint utilizes a relationship between forces and torques such as may be understood by reference to a simple lever model. As an initial matter, the approach used in the present methods are fundamentally different than the approach used in conventional haptic systems to express joint limits. In the present methods, the ROM limit problem is up-ended. Rather than considering what forces should be exert on the user when an ROM limit is hit, such as seen in a typical haptic system, the approaches described herein consider: "When one has a mechanism with these joints that are free to move (not at limit), what forces can the user exert on it?" To illustrate this point, consider a 7-DOF manipulator with 1 DOF at a ROM limit, and the other 6 DOFs non-redundant. The user can move in any desired direction, and it would seem that the user should not feel a force from this locked DOF.

B. Part 1: Simple Lever Model

Figure 20:
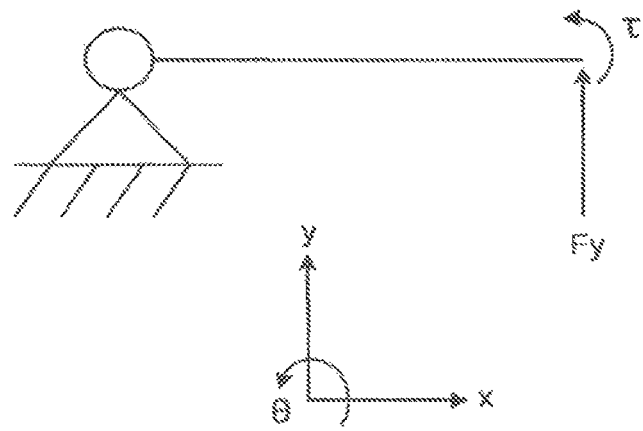
FIG. 20-23 illustrate example model relationships in the constraints within the inverse kinematics calculations that provide desired joint behaviors when a joint is at a range of motion limits.

In one aspect, methods for providing joint movement that expresses one or more joints are at a joint ROM limit utilize a constraint based on a relationship that would be seen between loads (e.g. force and torque) in a real-world physical model of the manipulator. In this example, the constraint is based on a relationship between force and torque as seen in a simple lever, such as shown in FIG. 20 as a handle rigidly mounted at one end. In this configuration, a force in the x direction (parallel to the lever) can always be applied, but in order to apply a force in the positive y direction, a clockwise torque is applied. Note the apparent conflict that the system is applying both the y force, and the torque that opposes it. If the opposing torque was not applied, then the lever would move, and the y force would not be able to be applied. Neglecting inertia and friction, it would be impossible to apply a force to something that moves out of the way when pushed. Therefore, the relationship between force and torque for this system, where positive torque is counter-clockwise, is as follows:

$$\tau = -F_y r \quad \text{(Equation 1)}$$

1. Emulating Force Relationship of Simple Lever with Min-SSE Inverse Kinematics

In certain embodiments, methods emulate this relationship in the simple lever model within the minimum SSE inverse kinematics of the manipulator system. For example, in a manipulator system having one freely movable joint, the Jacobian is as follows:

$$J = \begin{bmatrix} 0 \\ r \\ 1 \end{bmatrix}$$

Note that this is not necessarily a 1-DOF manipulator, but all other DOFs are at joint limits. For example, this may describe a 7-DOF planar manipulator with 6ODFs that have reached their respective joint limits.

One may want to determine what torque would be received from applying a force on the masters, which would be equivalent to applying a position displacement at the master, and seeing what the resulting position and orientation errors are. This problem can be solved in the general case as follows. Letting $X_G$ be a goal position (trans and rot) for the virtual slave, and $X_S$ be the stable position that the inverse kinematics algorithm has converged to, the goal position can be changed to $X_G + \Delta_G$, and the new stable position $X_S + \Delta_S$ can be solved. Assume that $\Delta_S$ is small enough that the Jacobian can be approximated as constant over this motion. $X_S + \Delta_S$ is a stable point meaning that the position error, applied to the J inverse, gives zero joint motion:

$$J^+(X_G + \Delta_G - X_S - \Delta_S) = 0$$

Distribute as:

$$J^+(X_G - X_S) + J^+(\Delta_G - \Delta_S) = 0$$

The first term is zero, since $X_S$ is the stable point for $X_G$, leaving:

$$J^+(\Delta_G - \Delta_S) = 0$$

$$J^+ \Delta_G = J^+ \Delta_S$$

$$J J^+ \Delta_G = J J^+ \Delta_S$$

Note that since $\Delta_S$ is actual motion of the virtual slave, i.e. motion within the allowable workspace lies in the column space of J. Note also that $J J^+$ is a projector onto the column space of J, so that $\Delta_S$ passes through unaffected: $\Delta_S = J J^+ \Delta_S$. Thus:

$$J J^+ \Delta_G = \Delta_S$$

Now this result is used to determine what torques result when a y-direction force is applied on the simple lever. Assume the masters are moved from their equilibrium position [r 0 0] to a position [r dy 0], the new equilibrium position for the virtual slave will be as follows:

$$\Delta_s = J J^+ \begin{bmatrix} 0 \\ dy \\ 0 \end{bmatrix}$$

where $$J^+ = (J^T J)^{-1} J^T = \left( [0 \ r \ 1] \begin{bmatrix} 0 \\ r \\ 1 \end{bmatrix} \right)^{-1} [0 \ r \ 1] = (r^2 + 1)^{-1} [0 \ r \ 1]$$

so $$\Delta_s = \frac{1}{r^2 + 1} \begin{bmatrix} 0 & 0 & 0 \\ 0 & r^2 & r \\ 0 & r & 1 \end{bmatrix} \begin{bmatrix} 0 \\ dy \\ 0 \end{bmatrix} = \frac{1}{r^2 + 1} \begin{bmatrix} 0 \\ dy \ r^2 \\ dy \ r \end{bmatrix}$$

If the original position is assumed to have had no error ($X_G = X_S$), then the error will now be:

$$err = \Delta_G - \Delta_s = \begin{bmatrix} 0 \\ dy \\ 0 \end{bmatrix} - \frac{1}{r^2 + 1} \begin{bmatrix} 0 \\ dy \ r^2 \\ dy \ r \end{bmatrix} = \begin{bmatrix} 0 \\ \frac{1}{r^2 + 1} \\ \frac{-r}{r^2 + 1} \end{bmatrix} dy$$

On the Master Tele-manipulator (MTM) side, the error gets converted to force and torque. Let the gains used for this conversion be:

$k_F$: MTM force gain, i.e. $F_{MTM} = k_F \ err_{pos}$
$k_T$: MTM torque gain, i.e. $\tau_{MTM} = k_T \ err_{rot}$ So then:

$$F_{MTM} = k_F \begin{bmatrix} 0 \\ \frac{dy}{r^2 + 1} \end{bmatrix}$$

$$\tau_{MTM} = k_T \frac{-r \ dy}{r^2 + 1}$$

Now the constraint from the simple lever (Equation 1) can be applied, and $k_F$ and $k_T$ are solved in order to make sure the MTM feedback emulates the mechanical system accurately:

$$\tau = -F_y r$$

$$k_T \frac{-r \ dy}{r^2 + 1} = -k_F \frac{dy}{r^2 + 1} r$$

$$k_T = k_F$$

Therefore, if these two gains are set equal, then the balance between force and torque will mimic the mechanical system that it is intended to emulate.

While it may seem somewhat surprising, this result is independent of the lever radius r. One set of parameters can be used for the algorithm, and it will enforce the proper force/torque relationship for any lever. This is because the lever radius is encoded in the curvature of the workspace boundary that the inverse kinematics loop is optimizing on. This curvature determines how much position error can be improved by sacrificing a certain amount of rotation error, which ultimately determines what combination of position and rotation error (thus force and torque) the inverse kinematics converges to. Note the gains $k_T$ and $k_F$ may be scaled up or down, which changes the stiffness of the constraint at the MTM to provide a desired behavior.

In another aspect, methods utilizing a simple lever type relationship can also incorporate scaling or weighting of certain joints or joint movements to provide a desired result. For example, it may be desired to account for the various scales (e.g. fine, normal, or quick) among one or more joint movements. Typically, it is desired to determine the effect of Cartesian weights on the balance between torque and force. The Cartesian weights adjust the weighting between translation and orientation when inverse kinematics finds the least-squares solution to the goal. One such derivation is shown below. W is the cartesian weighting matrix, which typically has the form, for a 6 DOF system:

$$W = \begin{bmatrix} w & & & & & \\ & w & & & & \\ & & w & & & \\ & & & 1 & & \\ & & & & 1 & \\ & & & & & 1 \end{bmatrix}$$

or for the present 3 DOF example:

$$W = \begin{bmatrix} w & & \\ & w & \\ & & 1 \end{bmatrix}$$

The weights can be applied to both the Jacobian and the error term that the inverse kinematics is minimizing, thus the stable point satisfies:

$(WJ)^+ W(X_G + \Delta_G - X_S - \Delta_S) = 0$ $(WJ)^+ W(\Delta_G - \Delta_S) = 0$ $(WJ)^+ W \Delta_G = (WJ)^+ W \Delta_S$ $WJ(WJ)^+ W \Delta_G = WJ(WJ)^+ W \Delta_S$ As in the previous section, $\Delta_S$ is motion of the virtual slave within the allowable workspace, so $\Delta_S$ is in the column space of J, and therefore $W \Delta_S$ is in the column space of W J. Further, $(WJ)(WJ)^+$ is a projector onto the column space of WJ, so $WJ(WJ)^+ W \Delta_S = W \Delta_S$. Making this substitution yields:

$WJ(WJ)^+ W \Delta_G = W \Delta_S$

Since W is invertible, it can be removed from both sides to obtain the solution for $\Delta_S$.

$J(WJ)^+ W \Delta_G = \Delta_S$

Next, the scaling may be incorporated. In this example, the simple lever relationship is emulated in the master space per the following equation:

$\alpha$ = master scale, i.e. $X_{slave} = \alpha X_{master}$

Assuming that the goal position (in the master space) moves from [r 0 0] to [r dy 0], on the slave side, this is seen as a move from [αr 0 0] to [αr α dy 0]. The new equilibrium position for the virtual slave can be determined with the following equations:

$$\Delta_s = J(WJ)^+ W \begin{bmatrix} 0 \\ \alpha \, dy \\ 0 \end{bmatrix}$$

First calculate $(WJ)^+$:

$$(WJ)^+ = ((WJ)^T WJ)^{-1}(WJ)^T = \left( [0 \ wr \ 1] \begin{bmatrix} 0 \\ wr \\ 1 \end{bmatrix} \right)^{-1} [0 \ wr \ 1]$$

$$(WJ)^+ = (w^2 r^2 + 1)^{-1} [0 \ wr \ 1]$$

Where W is assumed to have the form:

$$W = \begin{bmatrix} w & 0 & 0 \\ 0 & w & 0 \\ 0 & 0 & 1 \end{bmatrix}$$

To finish calculating $\Delta_S$:

$$\Delta_s = \begin{bmatrix} 0 \\ r \\ 1 \end{bmatrix} (w^2 r^2 + 1)^{-1} [0 \ wr \ 1] \begin{bmatrix} 0 \\ w \alpha \, dy \\ 0 \end{bmatrix}$$

$$\Delta_s = \frac{1}{(w^2 r^2 + 1)} \begin{bmatrix} 0 & 0 & 0 \\ 0 & wr^2 & r \\ 0 & wr & 1 \end{bmatrix} \begin{bmatrix} 0 \\ w \alpha \, dy \\ 0 \end{bmatrix}$$

$$\Delta_s = \frac{1}{(w^2 r^2 + 1)} \begin{bmatrix} 0 \\ w^2 r^2 \alpha \, dy \\ w^2 r \, \alpha \, dy \end{bmatrix}$$

It should be noted that the two terms differ in that one has $r^2$ and one has r. Thus, as can be seen above, the inverse kinematics converges in slave space. When sent back to the master, the positions get scaled by $1/\alpha$, but the orientation does not:

$$\Delta_{S\_MTM} = \frac{1}{(w^2 r^2 + 1)} \begin{bmatrix} 0 \\ w^2 r^2 dy \\ w^2 r \, \alpha \, dy \end{bmatrix}$$

Now the error is calculated in master space. As above, assuming the original position had no error ($X_G = X_S$), then:

$$err = \Delta_{G\_MTM} - \Delta_{S\_MTM} = \begin{bmatrix} 0 \\ dy \\ 0 \end{bmatrix} - \qquad \text{(Equation 2)}$$

$$\frac{1}{(w^2 r^2 + 1)} \begin{bmatrix} 0 \\ w^2 r^2 dy \\ w^2 r \, \alpha \, dy \end{bmatrix} = \begin{bmatrix} 0 \\ \frac{1}{w^2 r^2 + 1} \\ \frac{-w^2 r \, \alpha}{w^2 r^2 + 1} \end{bmatrix} dy$$

The MTM force and torque is the error, times the appropriate gain:

$$F_{MTM} = k_F \begin{bmatrix} 0 \\ 1 \\ \frac{1}{w^2 r^2 + 1} \end{bmatrix} dy$$

$$\tau_{MTM} = k_T \frac{-w^2 r \alpha}{w^2 r^2 + 1} dy$$

Once again, the intent is to emulate the simple lever, however, the lever has a radius r in slave scale. In the master scale, it appears as a lever of radius $r/\alpha$. Thus, the following is enforced:

$$\tau = -F_y \frac{r}{\alpha} \quad \text{(Equation 3)}$$

$$k_T \frac{-w^2 r \alpha}{w^2 r^2 + 1} dy = -k_F \frac{1}{w^2 r^2 + 1} dy \frac{r}{\alpha}$$

$$k_T w^2 \alpha^2 = k_F$$

Thus, if given $\alpha$, $k_T$, and $k_F$, then w can be chosen so that the desired relationship between force and torque is achieved. Note that once again, r drops out of the final equation, so the result is independent of the length of the lever.

2. Emulating Force Relationship of Simple Lever with Handlebar

In another aspect, methods may utilize the simple lever relationship using a slightly different derivation as needed for a desired purpose, such as for control of an endoscopic camera. In an example embodiment, the endoscopic camera is controlled using a "handlebar" in which force and torque are both determined by the force gain $k_F$. For reference, the following derivation shows how the Cartesian weight w can be adjusted to enforce the desired force/torque balance with the handlebar.

Figure 22:
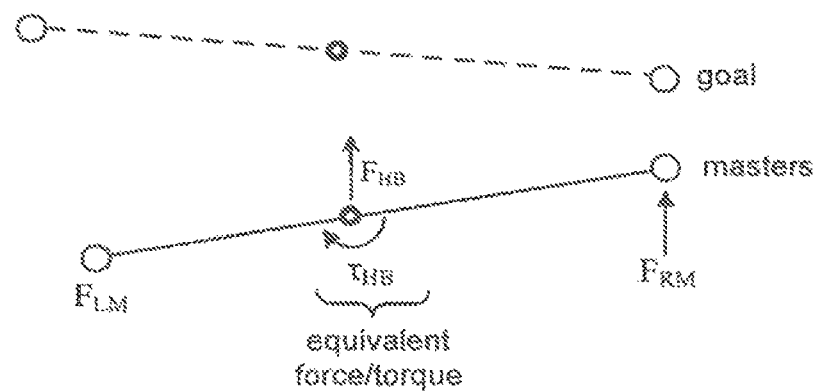

The camera control handlebar is shown in FIG. 22, which depicts the camera control handlebar and the forces on the masters and equivalent force/torque relationship. The handlebar radius is RHB in the master scale. Associated variables are defined as follows:

$err_{pos}$ and $err_{rot}$: position and rotation error in slave scale
$err_{LM}$ and $err_{RM}$: the corresponding position errors on left and right master, in master scale
$F_{LM}$, $F_{RM}$: forces felt on the masters due to $err_{LM}$ and $err_{RM}$
$F_{HB}$, $\tau_{HB}$: handlebar force and torque that are equivalent to the two forces $F_{LM}$ and $F_{RM}$
$R_{HB}$: the handlebar radius in master scale Note that the inverse kinematics optimizes movement based on translation and rotation, which the masters convert into left and right translation (forces); and the user synthesizes these left/right forces into perceived force and torque. In one aspect, the goal is to control the inverse kinematics' tradeoff between translation and rotation so that the user's perceived force and torque correctly obey the simple lever constraint (Equation 1).

First, the handlebar torque $\tau_{HB}$ is calculated. Because of superposition, the translational-induced forces on the masters can be ignored and just the rotation-induced forces considered. The $err_{rot}$ causes a position error of: $err_{rot} R_{HB}$ at each tip of the handlebar, where $R_{HB}$ is the handlebar radius (in master scale). This results in a force of:

$k_F \, err_{rot} \, R_{HB}$ which gives the equivalent torque:

$\tau_{HB} = 2R_{HB}(k_F err_{rot} R_{HB}) = 2k_F R_{HB}^2 err_{rot}$

Note the factor of 2, because there is a torque being applied at each end of the handlebar. Next $F_{HB}$, is calculated using superposition, this time ignoring the rotational effects on the master forces, and just calculating the translational: $err_{pos}$ creates an identical error on each handlebar end, which results in forces which sum up:

$F_{HB} = 2k_F err_{pos}$

Since in the master scale, the lever has an apparent radius $r/\alpha$, to enforce the constraint of the simple lever the following equation is used:

$\tau_{HB} = -F_{HB} r/\alpha$

Substituting Yields:

$2k_F R_{HB}^2 err_{rot} = -r 2k_F err_{pos}/\alpha$

Simplifying Yields:

$R_{HB}^2 err_{rot} = -r \, err_{pos}/\alpha$

From Equation 2, know that the inverse kinematics converges to:

$$err_{pos} = \frac{1}{w^2 r^2 + 1} dy$$

$$err_{rot} = \frac{-w^2 r \alpha}{w^2 r^2 + 1} dy$$

Substituting and Simplifying:

$$R_{HB}^2(w^2 r \alpha) = r/\alpha \quad \text{(Equation 4)}$$

$$w = \frac{1}{R_{HB} \alpha}$$

Note that RHB $\alpha$ is equal to the handlebar size in the slave scale, which can be can also be expressed as the control point radius (RCC). It should be noted that this is a radius, not a diameter.

$$w = \frac{1}{R_{CC}}$$

C. Part 2: Energy-Based Approach

Figures 21A, 21B:
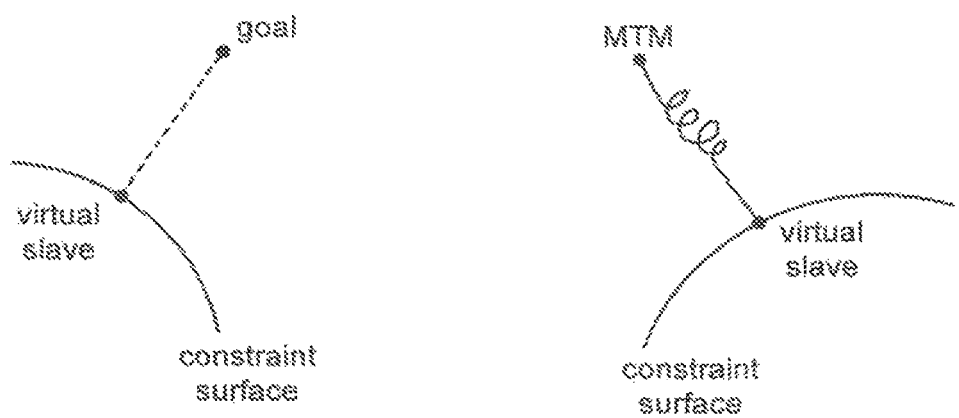

In a second approach, the system is modeled to emulate a virtual spring between the master and the slave and considers the energy stored in the virtual spring between the master and the slave. This approach generalizes to arbitrary degrees of freedom, without having to worry about the details of the mechanism. In some embodiments, this approach is simpler and is generalized to 6 DOF. In some methods, this approach may also utilize the constraint surface described herein, as shown in the example illustrated in FIGS. 21A-21B.

In one example of this approach, the following equations are used in which:

$X_G$ is the goal point: the position of the master, in the master scale
$X_S$ is the stable point: the position of the virtual slave in the master scale
$\alpha$=master scale factor, i.e. $X_{slave} = \alpha \, X_{master}$
poserr($X_G$, $X_S$, i): the i-th component of position error between $X_G$ and $X_S$ roterr($X_G$, $X_S$, i): the i-th component of rotation error between $X_G$ and $X_S$ Considering the virtual spring connecting $X_G$ to $X_S$ (in the master scale), the energy stored in the spring is $$E = \sum_{i=1,2,3} \frac{1}{2} k_F poserr(X_G, X_S, i)^2 + \sum_{i=1,2,3} \frac{1}{2} k_\tau roterr(X_G, X_S, i)^2$$

This quantity is similar to the sum-squared error that the inverse kinematics algorithm minimizes. This calculation happens on the slave side, so the scale factor is applied:

$$SSE = \sum_{i=1,2,3} (w_i \alpha poserr(X_G, X_S, i))^2 + \sum_{i=1,2,3} (w_{i+3} roterr(X_G, X_S, i))^2$$

From the above, it is clear that the inverse kinematics calculation converges to a position that minimizes the energy stored in the virtual spring, if and only if:

$$\frac{w_i^2 \alpha^2}{w_j^2} = \frac{k_F}{k_\tau} \; \forall \; i \in \{1, 2, 3\}, j \in \{4, 5, 6\} \qquad \text{(Equation 5)}$$

This same result is found in Equation 3, with the assumption that $w_j$=1. This shows that the described method generalizes beyond the simple lever used in the previous sections. In the face of constraints that may combine position and orientation, the virtual slave does precisely what a physical mechanism would do, minimizing energy in the virtual spring. Since the force/torque felt by the user is a function of the displacement of the virtual spring, this means that the force the user feels mimics a physical system as well.

D. Part 3: Conservation of Energy

The following points briefly highlight various aspects of these approaches in expressing joint ROM limits through calculated joint movements. In the simple lever approach described above, joint limits in the system create complex constraint surfaces that combine position and orientation, which can be difficult to express these to the user. Another manner in which to express these is to emulate a physical system as described herein. With the simple lever, the force/torque relationship model has been demonstrated. It was shown that the least-squares inverse kinematics algorithm can be used to emulate this force/torque relationship, if the parameters are set properly and the necessary equations were derived to deal with following scale, and uneven $k_F$ and $k_\tau$ on the master. With this energy-based approach, the method generalizes to arbitrary mechanisms in 6-DOF space. The minimum SSE inverse kinematics described emulate exactly what a physical system would do, minimizing the energy stored in the virtual spring on the master. When considering conservation of energy, differentially, the methods consider not only the point to which the inverse kinematics converge to, but also what path taken to get to that point. Movement along this path can be controlled by including a surface constraint so that the joints move along a particular surface so as to provide a desired behavior, for example creating a surface that obeys conservation of energy so that movement along the path appears more natural.

As demonstrated in the above sections, the minimum SSE inverse kinematics is sufficient to provide a "natural" feel in expression of the joint ROM limits and the following section illustrates that under certain assumptions, which include conservation of energy, that it is the only satisfactory algorithm.

1. Conservation of Energy in Virtual Slave Motion

While the above example is concerned largely with what point the inverse kinematics algorithm converges to, this section illustrates how conservation of energy places a constraint on the steps that the inverse kinematics take while converging. Of particular importance, providing a constraint that adheres to the conservation of energy to avoid the counter-intuitive movements discussed above—namely, pushing with a small force and receiving a relatively large torque in return. In one aspect, during following, the master (user) can add or remove energy from the virtual spring connecting the master to the virtual slave. In one aspect, the virtual slave should never move in a way that adds energy to the virtual spring. This can be seen as a statement of passivity and is graphically illustrated in FIG. 23 and detailed further in the equations below.

To formalize this statement, the following equations may be used, for which the definitions are:

$X_G(t)$ the goal point: the position of the master, in the master scale $X_{VS}(t)$ the virtual slave position in the master scale. Note that the inverse kinematics algorithm may not have converged.

$\alpha$=master scale factor, i.e. $X_{slave} = \alpha \, X_{master}$ (v, ω) he virtual slave velocity, in the master scale (F, τ) the force and torque (in the master scale) of the virtual spring acting on the master, which is opposite the force acting on the virtual slave.

The statement of conservation of energy is:

$$-F \cdot v - \tau \cdot \omega \leq 0$$

$$F \cdot v + \tau \cdot \omega \geq 0 \qquad \text{(Equation 1)}$$

Figure 23:
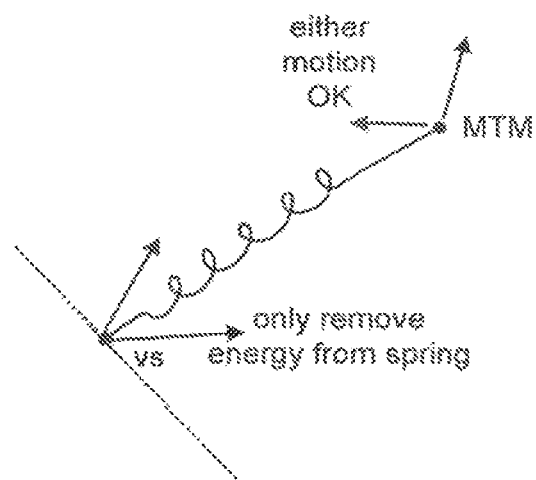
Figure 24:
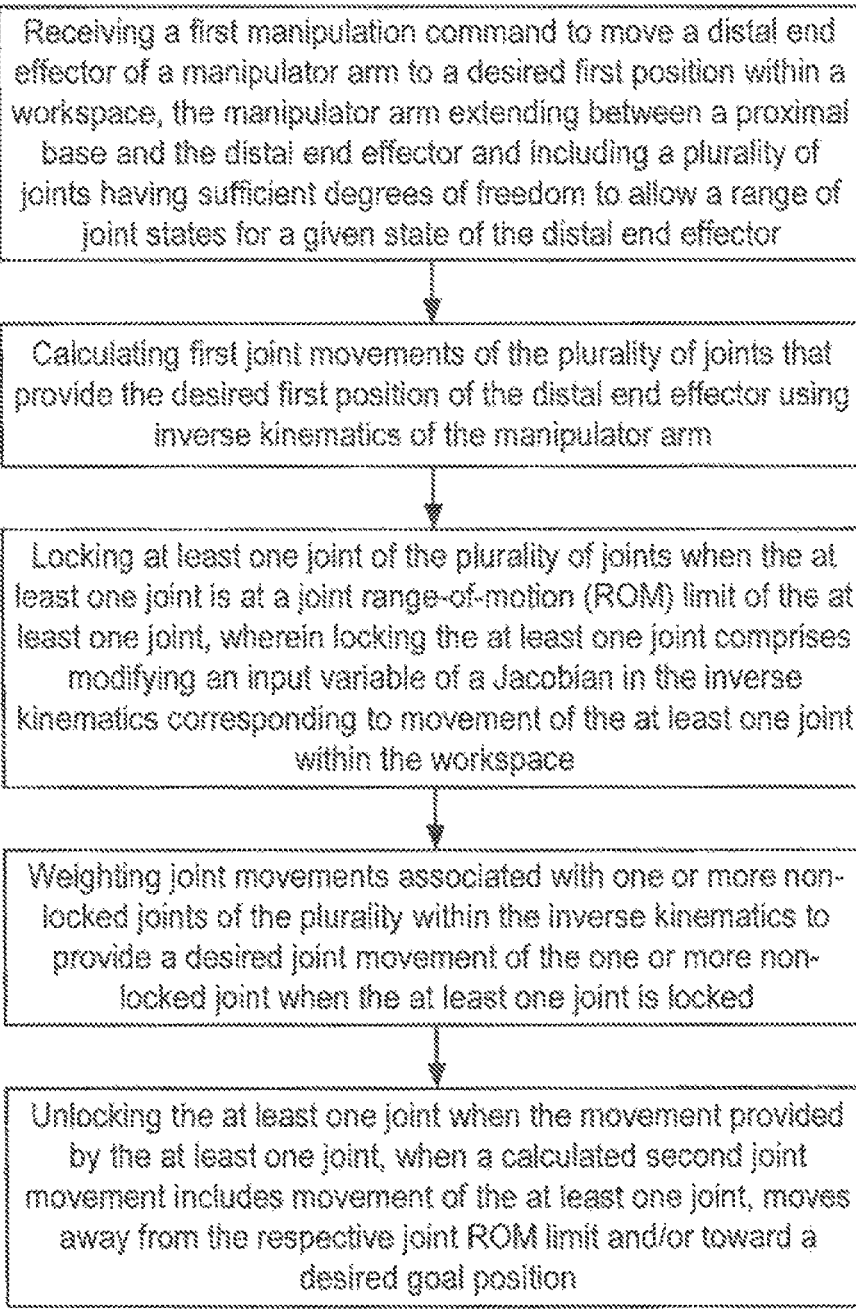
FIG. 24-25 illustrate methods in accordance with embodiments of the invention.
Figure 25:
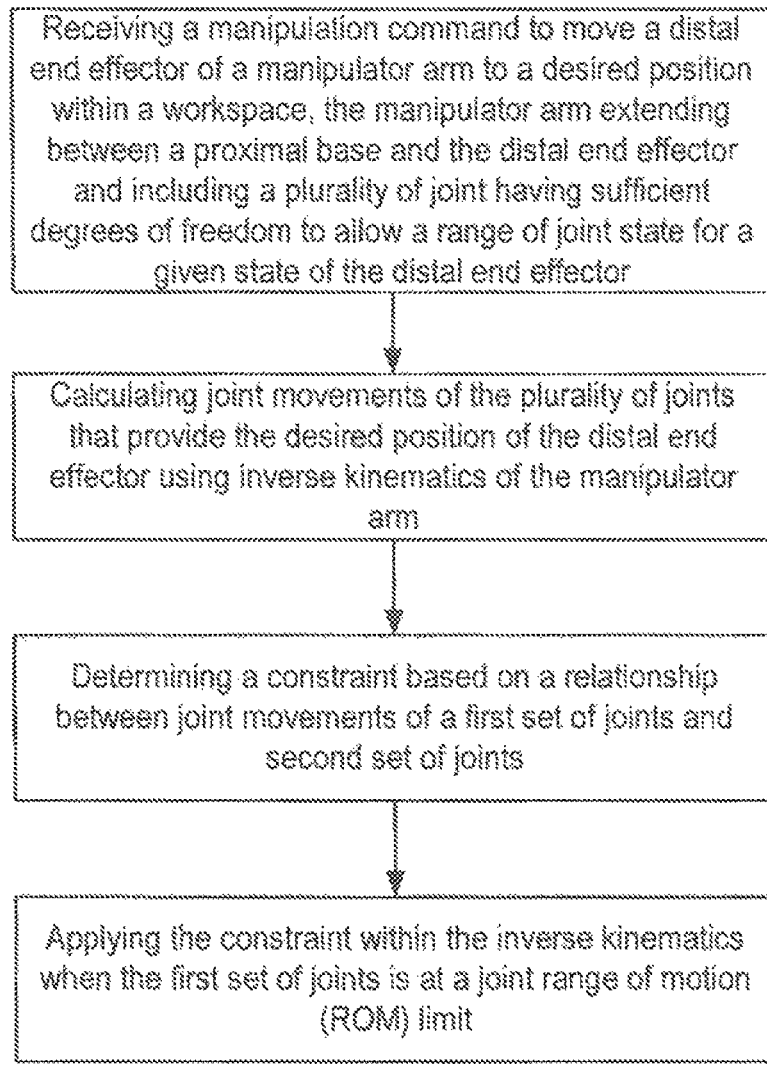

Note that the FIG. 23 portrays only translation, but the math includes translation and orientation. Note also that F and τ are proportional to (i.e. in the same direction as) the Cartesian error vector. This error vector determines the "cartvel" vector that is the desired inverse kinematics step, and v and ω are the inverse kinematics step that is achieved after application of the pseudoinverse. The pseudoinverse should give an output vector that has a positive dot product with the input vector, thereby obeying the conservation of energy.

In this derivation, it is of particular interest to distinguish between the master side (with master scale) and the slave side (with slave scale), given the intent to obey conservation of energy on the master side.

Assume that in calculating cartvel, the input to the pseudoinverse, as:

$$cartvel = W \begin{bmatrix} \alpha poserr(X_G, X_{VS}, t) \\ roterr(X_G, X_{VS}, t) \end{bmatrix}$$

Note that $\alpha \, poserr(X_G, X_{VS}, t)$ is the poserr calculated on the slave side. Next, the pseudoinverse matrix $(WJ)^+$ is applied to cartvel to get a set of joint velocities. The Jacobian is then applied to convert joint velocities back into cartesian velocity:

$$\begin{bmatrix} \alpha v \\ \omega \end{bmatrix} = J(WJ)^+ W \begin{bmatrix} \alpha poserr(G, VS, t) \\ roterr(G, VS, t) \end{bmatrix}$$

Multiply W by both sides:

$$W \begin{bmatrix} \alpha v \\ \omega \end{bmatrix} = WJ(WJ)^+ W \begin{bmatrix} \alpha poserr(G, VS, t) \\ roterr(G, VS, t) \end{bmatrix}$$

$WJ(WJ)^+$ is a projector onto the column space of WJ: the input and output of this projection have positive (or zero) dot product:

$$W \begin{bmatrix} \alpha v \\ \omega \end{bmatrix} \cdot W \begin{bmatrix} \alpha poserr(G, VS, t) \\ roterr(G, VS, t) \end{bmatrix} \geq 0$$

For W, substitution of the recommendation of 1 for orientation weights and $$w = \frac{\sqrt{k_f}}{\alpha \sqrt{k_\tau}}$$

(see Equation 3) for position weights yields:

$$\begin{bmatrix} \sqrt{k_f/k_\tau} \, v \\ \omega \end{bmatrix} \cdot \begin{bmatrix} \sqrt{k_f/k_\tau} \, poserr(G, VS, t) \\ roterr(G, VS, t) \end{bmatrix} \geq 0$$

$$\begin{bmatrix} v \\ \omega \end{bmatrix} \cdot \begin{bmatrix} \frac{k_f}{k_\tau} poserr(G, VS, t) \\ roterr(G, VS, t) \end{bmatrix} \geq 0$$

$$\begin{bmatrix} v \\ \omega \end{bmatrix} \cdot \begin{bmatrix} k_f poserr(G, VS, t) \\ k_\tau roterr(G, VS, t) \end{bmatrix} = \begin{bmatrix} v \\ \omega \end{bmatrix} \cdot \begin{bmatrix} f \\ \tau \end{bmatrix} \geq 0$$

Therefore, conservation of energy will be maintained if the Cartesian weights are set as recommended. If not the weights are not set as recommended, the weighting between position and orientation will be off, and there may likely be situations where there is too much of one or the other, such that energy is not conserved, which in turn, may result in movement that seems "unnatural" or counter-intuitive. For example, one simple mistake that can be made and result in failing the conservation of energy condition, is to calculate rotation error in units other than radians (e.g. off by a factor of 2), such that the rotation error will be scaled incorrectly with respect to position error.

2. Minimum SSE Inverse Kinematics Only Algorithm that Obeys Conservation of Energy In the example described above, it was shown that Minimum SSE Inverse kinematics does what a real physical system would do: minimize energy stored in the spring between master and virtual slave. While various algorithms could be used to mimic physical systems, since many manipulator systems include sufficient degrees of freedom to move in ways that don't change energy, i.e. is contours, use of the minimum SSE inverse kinematics is particularly advantageous since under certain assumptions, no other algorithm can minimize the virtual spring energy and still obey the conservation of energy constraint. These assumptions are first that Xs is function of Xg; that there is no hysteresis (e.g. synthetic friction on the constraint surface); and that the algorithm is assumed to converge instantly. Next, it is assumed that $X_S(X_G)$ makes no discrete jumps (e.g. from one local maximum to another); as one moves, $X_G$, $X_S$ moves continuously.

In one aspect, the Cartesian space that $X_G$ exists in can be divided into two sets:
  W: the reachable workspace
  U: the unreachable space
  * Assuming that $X_S = X_G$ for all $X_G$ in W Note that this assumption, combined with the conservation of energy constraint, means that if $X_G$ is outside of W, the corresponding $X_S$ will be on the boundary of W. Otherwise, when drawing a straight line between $X_G$ and $X_S$, the goal moves along this line from the boundary of W to $X_G$, the stable point would move in a way to increase the stretch of the spring. Considering a goal-point path $X_G(t)$ and corresponding stable-point path $X_S(t)$ in the reachable workspace. The conservation of energy constraint (Equation 1) can be written as:

$$\begin{bmatrix} poserr(X_G(t), X_S(t)) \\ roterr(X_G(t), X_S(t)) \end{bmatrix} \cdot \frac{dX_s(t)}{dt} \leq 0$$

But the equation should also hold if you travel the path in the opposite direction, which gives the same equation, with ≤ replaced by ≥, so that ultimately, $$\begin{bmatrix} poserr(X_G(t), X_S(t)) \\ roterr(X_G(t), X_S(t)) \end{bmatrix} \cdot \frac{dX_s(t)}{dt} \leq 0$$

This result indicates that as t increases, $X_S(t)$ is either stationary, or moving perpendicular to the vector $X_G(t)-X_S(t)$. When $X_G$ is outside of W, its corresponding $X_S$ is the closest point in W to $X_G$, or the conservation of energy constraint will be violated. The point is "closest" is in the sense of the norm that the minimum SSE inverse kinematics minimize, (e.g. there is a weighting between position and rotation according to the Cartesian weights as described previously).

Let a goal point $X_{G1} \in U$ be given, with corresponding stable point $X_{S1} \in W$. Let $X_{C1}$ be the closest point in W to $X_{G1}$, and assume that $|X_{G1}-X_{S1}|>|X_{G1}-X_{C1}|$. Consider a straight-line path $X_G(t)$ such that $X_G(0)=X_{C1}$ and $X_G(1)=X_{G1}$. Then the corresponding $X_S(t)$ satisfies $X_S(0)=X_{C1}$ and $X_S(1)=X_{S1}$. Since $X_S(1)$ is further from $X_{G1}$ than $X_S(0)$ is, then at some point d $X_S(t)/dt$ must not be perpendicular to poserr($X_G(t)$, $X_S(t)$). This violates the conservation of energy constraint.

3. Applicable Algorithms

Given this proof, it is appreciated that there are a number of viable algorithms, other than these exact equations, that would obey the conservation of energy that could be used in accordance with methods of the invention. For example, below are a few such alternative algorithms:

Synthetic friction on constraint surfaces: This features makes the constraint surface a bit less slippery. This breaks the first assumption of the proof: $X_S$ is no longer a "strict" function of $X_G$; there is some hysteresis in the motion of $X_S$.

Soft Edges. Another conceivable algorithm would involve "soft" edges to the workspace, where $X_S$ falls off of $X_G$ gradually, rather than making a hard stop at the workspace edge. This breaks our assumption that $X_G$ maps to $X_S$ everywhere in W.

While the example embodiments have been described in some detail for clarity of understanding and by way of example, a variety of adaptations, modifications, and changes will be obvious to those of skill in the art. It is appreciated that various aspects of the example embodiments described herein may be combined in accordance with the principles of the invention described herein. Hence, the scope of the present invention is limited solely by the appended claims.

What is claimed is:

1. A system comprising:
    a manipulator arm coupled to a proximal base, the manipulator arm configured to support an end effector and robotically move the end effector relative to the proximal base, the manipulator arm having a plurality of joints between the end effector and the proximal base; and
    a processor configured to:
        calculate joint movements of the plurality of joints that provide a desired position of the end effector using inverse kinematics of the manipulator arm; and
        when a first set of one or more joints of the plurality of joints is at corresponding joint range of motion (ROM) limits:
            determine a constraint based on a relationship between joint movement of the first set and a second set of one or more joints of the plurality of joints; and
            apply the constraint within the inverse kinematics to provide haptic feedback to a user.

2. The system of claim 1, wherein the relationship is between a translational movement of the first set and a rotational joint movement of the second set.

3. The system of claim 1, wherein the relationship is based on a relationship of static loads on the first set and the second set when the first set reaches the corresponding joint ROM limits.

4. The system of claim 1, wherein to apply the constraint, the processor is configured to impose, to a Jacobian, at least one of a scaling and a weighting.

5. The system of claim 1, wherein the constraint comprises a first kinetic energy of the first and second sets being substantially the same as a second kinetic energy of the first and second sets, the first kinetic energy being when the first set reaches the corresponding joint ROM limits and the second kinetic energy being within the calculated joint movements in which the first set remain at the corresponding joint ROM limits.

6. The system of claim 1, wherein the first and second sets, in combination, comprise all of the plurality of joints of the manipulator arm.

7. The system of claim 1, wherein to determine the constraint, the processor is configured to model a virtual spring between a master and a slave of the manipulator arm.

8. The system of claim 1, wherein the constraint comprises a constraint surface.

9. The system of claim 8, wherein the processor is further configured to:
    apply a synthetic friction to the constraint surface so as to resist movement of one or more joints along the constraint surface when the first set is at the corresponding joint ROM limits.

10. The system of claim 8, wherein the processor is further configured to:
    modify a stiffness of one or more joints along the constraint surface when the first set is at the corresponding joint ROM limits.

11. The system of claim 1, wherein the system is a tele-operation surgical system.

12. The system of claim 1, wherein the plurality of joints has sufficient degrees of freedom to allow a range of joint states for a given position of the end effector.

13. A method comprising:
    receiving a manipulation command to move an end effector supported by a manipulator arm to a desired position within a workspace, the manipulator arm extending between a proximal base and the end effector;
    calculating joint movements of one or more joints of a master control corresponding to calculated joint movement of a plurality of joints of the manipulator arm using inverse kinematics of the manipulator arm; and
    when a first set of one or more joints of the plurality of joints is at corresponding joint range of motion (ROM) limits:
        determining a constraint based on a relationship between joint movement of the first set and a second set of one or more joints of the plurality of joints; and
        applying the constraint within the inverse kinematics to provide haptic feedback to a user.

14. The method of claim 13, wherein the relationship is between a translational joint movement of the first set and a rotational joint movement of the second set.

15. The method of claim 13, wherein applying the constraint further comprises imposing, to a Jacobian, at least one of a scaling and a weighting.

16. The method of claim 13, wherein the determining the constraint comprises modeling a virtual spring between a master and a slave of the manipulator arm.

17. The method of claim 13, wherein the constraint comprises a first kinetic energy of the first and second sets when the first set reaches the corresponding joint ROM limits being substantially the same as a second kinetic energy of the first and second sets within the calculated joint movements in which the first set remains at the corresponding joint ROM limits.

18. The method of claim 13, wherein the constraint comprises a constraint surface.

19. The method of claim 18, further comprising:
    applying a synthetic friction to the constraint surface so as to resist movement of one or more joints along the constraint surface when the first set is at the corresponding joint ROM limits; or
    modifying a stiffness of one or more joints along the constraint surface when the first set is at the corresponding joint ROM limits.

20. The method of claim 13, wherein the plurality of joints has sufficient degrees of freedom to allow a range of joint states for a given position of the end effector.

* * * * *

UNITED STATES PATENT AND TRADEMARK OFFICE
CERTIFICATE OF CORRECTION

PATENT NO. : 10,617,480 B2  
APPLICATION NO. : 16/201887  
DATED : April 14, 2020  
INVENTOR(S) : Gabriel F. Brisson Page 1 of 1

It is certified that error appears in the above-identified patent and that said Letters Patent is hereby corrected as shown below:

On the Title Page

Item (63) Related U.S. Application Data:
Please delete "Continuation of application No. 15/126,967, filed as application No. PCT/US2015/020889 on Mar. 17, 2015, now Pat. No. 10,188,471." and insert --Continuation of application No. 15/126,967, filed on Sep. 16, 2016, now Pat. No. 10,188,471, which is a 371 of application No. PCT/US2015/020889, filed on Mar. 17, 2015.--;

Item (56) References Cited:
Please delete "1,018,847 A1 1/2019 Brisson et al." and insert --10,188,471 A1 1/2019 Brisson et al.--.

Signed and Sealed this  
Twenty-sixth Day of May, 2020

Andrei Iancu  
*Director of the United States Patent and Trademark Office*